United States Patent

Bokelman et al.

[11] Patent Number: 5,966,218
[45] Date of Patent: Oct. 12, 1999

[54] BOBBIN OPTICAL INSPECTION SYSTEM

[75] Inventors: Gordon H. Bokelman; Thomas A. Fletcher, both of Chesterfield; Harold T. Hinson, Farnham; Steven F. Spiers, Richmond; Yeu-Hwa Shyy, Fairfax; Timothy F. Gacek, McLean, all of Va.

[73] Assignee: Philip Morris Incorporated, New York, N.Y.

[21] Appl. No.: 08/893,500

[22] Filed: Jul. 11, 1997

[51] Int. Cl.$^6$ .................................................. G01N 21/84
[52] U.S. Cl. ............................................................. 356/429
[58] Field of Search ..................... 356/429, 430, 356/431, 427; 131/907, 908; 348/88

[56] References Cited

U.S. PATENT DOCUMENTS

| | | |
|---|---|---|
| 3,089,497 | 5/1963 | Molins et al. . |
| 3,588,513 | 6/1971 | Akamatsu et al. . |
| 3,818,223 | 6/1974 | Gibson et al. . |
| 3,955,584 | 5/1976 | Molins et al. . |
| 4,001,579 | 1/1977 | Lebet et al. . |
| 4,011,950 | 3/1977 | McLoughlin et al. . |
| 4,054,377 | 10/1977 | Gibson . |
| 4,090,794 | 5/1978 | Benini . |
| 4,099,884 | 7/1978 | Nash . |
| 4,212,541 | 7/1980 | Ducommun et al. . |
| 4,238,994 | 12/1980 | Koch . |
| 4,266,674 | 5/1981 | Bell et al. . |
| 4,377,743 | 3/1983 | Bolt et al. . |
| 4,398,546 | 8/1983 | Fisher et al. . |
| 4,423,742 | 1/1984 | Reuland . |
| 4,645,921 | 2/1987 | Heitmann et al. . |
| 4,671,663 | 6/1987 | Sick . |
| 4,682,038 | 7/1987 | Focke . |
| 4,718,026 | 1/1988 | Long et al. . |
| 4,756,317 | 7/1988 | Edwards . |
| 4,766,315 | 8/1988 | Hellstrom et al. . |
| 4,767,924 | 8/1988 | Giebel et al. . |
| 4,776,351 | 10/1988 | Wahle et al. . |
| 4,805,641 | 2/1989 | Radzio et al. . |
| 4,841,763 | 6/1989 | Kang et al. . |
| 4,845,374 | 7/1989 | White et al. . |
| 4,860,772 | 8/1989 | Hensgen et al. . |
| 4,865,054 | 9/1989 | Lorenzen et al. . |
| 4,875,494 | 10/1989 | Siems . |
| 4,879,000 | 11/1989 | Gausa . |
| 4,906,099 | 3/1990 | Casasent . |
| 4,907,607 | 3/1990 | Focke et al. . |
| 4,915,827 | 4/1990 | Rosenthal . |
| 4,926,886 | 5/1990 | Lorenzen et al. . |
| 4,941,482 | 7/1990 | Heitmann et al. . |
| 4,963,743 | 10/1990 | Satake et al. . |
| 4,976,544 | 12/1990 | Neri . |
| 4,982,104 | 1/1991 | Yvito .................................. 356/430 |

(List continued on next page.)

OTHER PUBLICATIONS

"More Feedback: Process Control Leaps Ahead With New ABB Solutions [For Tobacco Manufacturing]", Tobacco Reporter (Nov. 1994) vol. 121, No. 11, p. 26, Doolittle, David E.

*Primary Examiner*—Richard A. Rosenberger
*Attorney, Agent, or Firm*—Burns, Doane, Swecker & Mathis, LLP

[57] ABSTRACT

A rewinder machine optically inspects banded paper unwound from a first bobbin by directing an elongated beam of light laterally across the paper. The elongated beam impinges the surface of the paper and forms reflections. A line scan camera containing a linear CCD array receives the reflections and generates output signals. A line scan processor processes the output signals to generate data indicative of the spacing between bands, the width of the bands, and the contrast of the bands. These calculations may be periodically transferred to a separate computer workstation over a network. The workstation generates statistical reports on the basis of the calculations, such as the band width, band spacing and band contrast as a function of lane number, and as a function of time. After being inspected by the camera, the paper is rewound on a rewind bobbin. Various mechanical features of the rewind machine allow rapid mounting and removal of bobbins of paper, and provide for high speed operation.

34 Claims, 16 Drawing Sheets

U.S. PATENT DOCUMENTS

| | | |
|---|---|---|
| 4,986,285 | 1/1991 | Radzio et al. . |
| 5,000,323 | 3/1991 | Cahill et al. . |
| 5,006,722 | 4/1991 | Adelson . |
| 5,010,904 | 4/1991 | Lassiter . |
| 5,013,905 | 5/1991 | Neri . |
| 5,024,333 | 6/1991 | Brink et al. . |
| 5,061,063 | 10/1991 | Casasent . |
| 5,072,128 | 12/1991 | Hayano et al. . |
| 5,086,279 | 2/1992 | Wochnowski et al. . |
| 5,118,195 | 6/1992 | Dobbie . |
| 5,150,175 | 9/1992 | Whitman et al. ................ 356/429 |
| 5,166,748 | 11/1992 | Dahlquist . |
| 5,189,708 | 2/1993 | Cox et al. . |
| 5,208,870 | 5/1993 | Ennis . |
| 5,223,915 | 6/1993 | Neri . |
| 5,228,462 | 7/1993 | Osmalov et al. . |
| 5,235,649 | 8/1993 | Reda . |
| 5,237,621 | 8/1993 | Cox et al. . |
| 5,243,408 | 9/1993 | Whitman, III . |
| 5,305,392 | 4/1994 | Longest, Jr. et al. . |
| 5,341,824 | 8/1994 | Fletcher et al. . |
| 5,345,955 | 9/1994 | Clearman et al. . |
| 5,353,357 | 10/1994 | Longest, Jr. et al. . |
| 5,365,596 | 11/1994 | Dante et al. . |
| 5,366,096 | 11/1994 | Miller . |
| 5,406,376 | 4/1995 | Maiwaid et al. . |
| 5,410,396 | 4/1995 | Rochester . |
| 5,414,270 | 5/1995 | Henderson et al. . |
| 5,426,509 | 6/1995 | Peplinski . |
| 5,432,600 | 7/1995 | Grollimund et al. . |
| 5,448,365 | 9/1995 | Grollimund et al. . |
| 5,534,114 | 7/1996 | Cutright et al. . |
| 5,641,971 | 6/1997 | Prigent ................ 356/430 |
| 5,718,249 | 2/1998 | Suzuki et al. . |
| 5,746,225 | 5/1998 | Okumoto et al. . |
| 5,762,075 | 6/1998 | Hoppe et al. . |

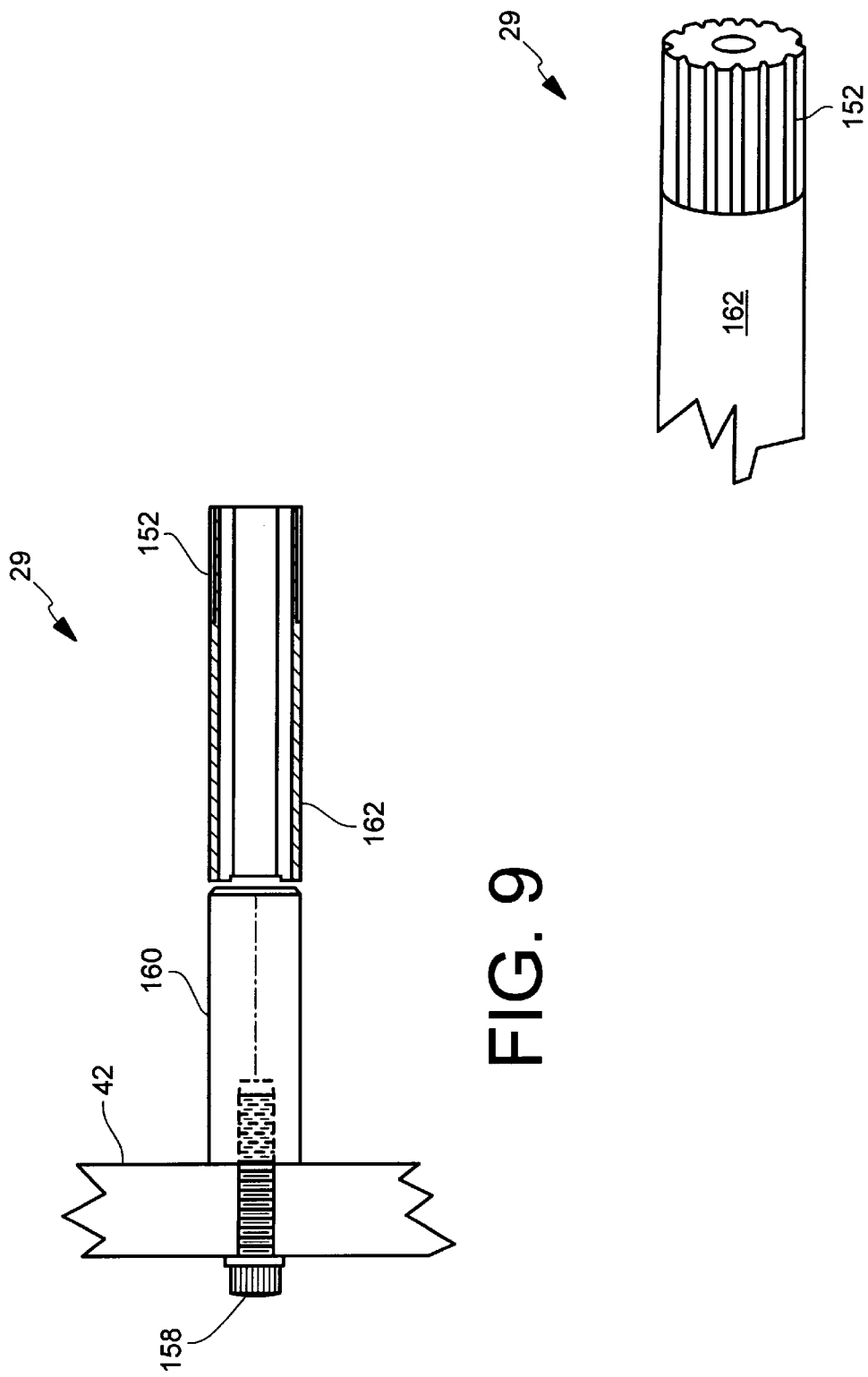

BOBBIN OPTICAL INSPECTION SYSTEM

CROSS REFERENCE TO RELATED APPLICATIONS

The present application is related to commonly assigned Ser. No. 08/893,538 entitled "Optical Inspection System for the Manufacture of Banded Cigarette Paper" and Ser. No. 08/893,505 entitled "Cigarette Making Machine Including Inspection of Paper Containing Bands", both of which were filed on the same date as the present application. Both of these applications are hereby incorporated by reference in their entireties.

BACKGROUND

The present invention relates generally to a system and method for inspecting a bobbin of paper containing bands.

Systems are known in the art which unwind a first bobbin of sheet-like material (referred to as the unwind bobbin), inspect the surface of the sheet-like material, and rewind the sheet-like material onto a second bobbin (referred to as the rewind bobbin). The inspection may entail projecting electromagnetic radiation on a moving web of material. The light impinges on the surface of the moving web, where it is reflected and received at a detector device. Any anomalies in the moving web can be detected by investigating the nature of the reflected electromagnetic radiation. For instance, a tear, pinhole or blemish in the web will manifest itself in a spike in the signal level from the detector (which is attributed to an increase or decrease in reflected radiation). This spike can be viewed by connecting the detector output to an oscilloscope, as exemplified by U.S. Pat. No. 5,426,509 to Peplinkski.

The prior art rewind/inspection machines suffer a number of drawbacks. First, the prior art rewind/inspection machines are not configured to allow the operator to quickly install and remove the unwind and rewind bobbins. This is a significant factor when many bobbins must be inspected in the course of each day.

Furthermore, these machines can apply considerable tension to the web of material as it passes from the unwind bobbin to the rewind bobbin, and are therefore ill-suited for particularly fragile sheet-like material. Cigarette paper, for example, is relatively weak, making it difficult to rewind a large bobbin at high speeds without breakage. Also, cigarette paper is relatively thin, making it difficult to evenly and cleanly rewind the paper onto the rewind bobbin.

The inspection of cigarette paper presents other challenges which the prior art has not addressed. FIG. 1, for instance, shows a cigarette 360 including cigarette paper 362 containing a plurality of bands 364 formed by depositing a layer of cellulosic pulp (or other material) on the base cigarette paper 362. FIG. 2 shows a section from a bobbin of cigarette paper containing these bands. Bands formed on cigarette paper often have reflective properties similar to the cigarette paper itself. Often, for instance, the bands are formed of white colored material which is difficult to distinguish from the white colored cigarette paper. Moreover, the basis weight of a bobbin of cigarette paper may vary along the length of the paper (due to the difficulty in maintaining a constant pulp application rate during the manufacture of the paper). The variance in basis weight of the paper influences its reflective properties, thereby obfuscating the differences between banded and non-banded regions, which are subtle enough to begin with. The prior art devices do not have the ability to interpret a reflection from a web of this nature. As mentioned, these devices are configured to examine a web surface for tears, pinholes and blemishes which manifest themselves in dramatic spikes in the video camera signal.

Also, with reference to FIG. 2, the operator may be interested in determining whether the width 372 of the bands, contrast of the bands, and distance 370 between bands is within proper tolerances. Whether a band width is too long, too short, or separated from its neighboring band by more or less than a desired distance can not be determined by simply observing the properties of a single point on a moving web. Rather, the properties of a band should be gauged by determining the spatial relationship between different elements on the web. As such, the prior art which only examines local points on the web is unsuited for the task of inspecting cigarette paper containing bands.

Pattern recognition techniques are one way of determining the spatial relationship between different features on a printed web of material. In a common technique, a camera forms a digital image of a portion of a web of material and information printed thereon. The digital image is then compared with a pre-stored template representing an error-free web portion. Discrepancies between the template and the image represent an irregular web. These techniques offer accuracy, but unfortunately entail a great deal of data processing. These techniques are therefore ill-suited for the task of detecting the properties of bands on a web moving at the high speeds required in a rewinder machine.

Accordingly, it is an exemplary objective of the present invention to provide a rewind/inspection machine which does not suffer from the above noted drawbacks.

SUMMARY

These and other exemplary objectives are achieved according to the present invention through a rewinder machine which enables an operator to easily and quickly mount and remove bobbins, and once activated, applies a constant tension on the bobbin paper. As the paper passes from the unwind bobbin to the rewind bobbin, one or more inspection stations analyze the properties of the paper. In the context of cigarette paper, the inspection stations can detect the spacing of bands, the width of the bands, and the contrast of the bands.

More specifically, the inspection system according to exemplary aspects of the present invention includes an unwind spindle assembly for mounting a first bobbin of paper. The paper from the first bobbin is passed over an inspection roller where it is illuminated by a light distribution assembly. Specifically, the light distribution assembly directs a stripe of light across the web. The stripe of light is reflected at the paper surface and then received at a line scan camera containing a linear charge coupled device (CCD) array.

The data from the CCD array is fed to a line scan processor. The line scan processor divides the data into a plurality of lanes. A single pixel from each lane is then compared with a variable threshold value to determine whether the lane corresponds to a band region or a non-band region. The pixel chosen within each lane changes from scan line to scan line to define a zig-zag pattern. By monitoring and recording successive pixels from each lane, the line scan processor is able to independently compute for each lane the width of bands on the web, the spacing between bands, and the average contrast of the bands.

The threshold used to discriminate band regions from non-band regions is dynamically set on the basis of moving averages of immediately preceding band regions and non-band regions. In one embodiment, the threshold represents the moving average of non-band background plus the greater of: (1) a set constant value (such as 10 gray levels) or (2) 50% of the moving average of banded region peak heights (where the "peak heights" correspond to the gray level of the banded region minus the gray level of a neighboring non-banded region). Dynamically setting the threshold in this manner accommodates a wide variety of different types of cigarette paper and band material, and also can account for changes in the basis weight of the paper along the length of the paper.

On periodic intervals, the information calculated by the line scan processor is assembled into an Ethernet packet and transferred over an Ethernet network to a computer workstation. The computer workstation then aggregates the packet with previously received packets and displays various summary statistical displays for the operator. For instance, the display provides graphs illustrating the band width, band spacing, band contrast, and band anomalies as a function of lane number for a reporting interval. Furthermore, the display presents cumulative statistics by presenting a graph of the band width, band spacing and band contrast as a function of time.

Once the paper has been inspected by the line scan camera, it is rewound on a second bobbin mounted on a rewind spindle assembly. A strain gauge sensor measures the tension applied to the paper as it is fed from the first bobbin to the second bobbin. The output of the strain gauge sensor is used to control resistance applied to the unwind spindle assembly, to provide constant tension to the paper and thereby reduce the possibility of paper breakage.

BRIEF DESCRIPTION OF THE DRAWINGS

The foregoing, and other, objects, features and advantages of the present invention will be more readily understood upon reading the following detailed description in conjunction with the drawings in which:

FIGS. 9 and 10 show an inspection roller for use in the rewinder machine of FIG. 3;

DETAILED DESCRIPTION

In the following description, for purposes of explanation and not limitation, specific details are set forth in order to provide a thorough understanding of the invention. However it will be apparent to one skilled in the art that the present invention may be practiced in other embodiments that depart from these specific details. In other instances, detailed descriptions of well-known methods, devices, and circuits are omitted so as not to obscure the description of the present invention with unnecessary detail. In the Figures, like numbers designate like parts.

1. Overview of the operation of the rewinder machine.

Figure 3:
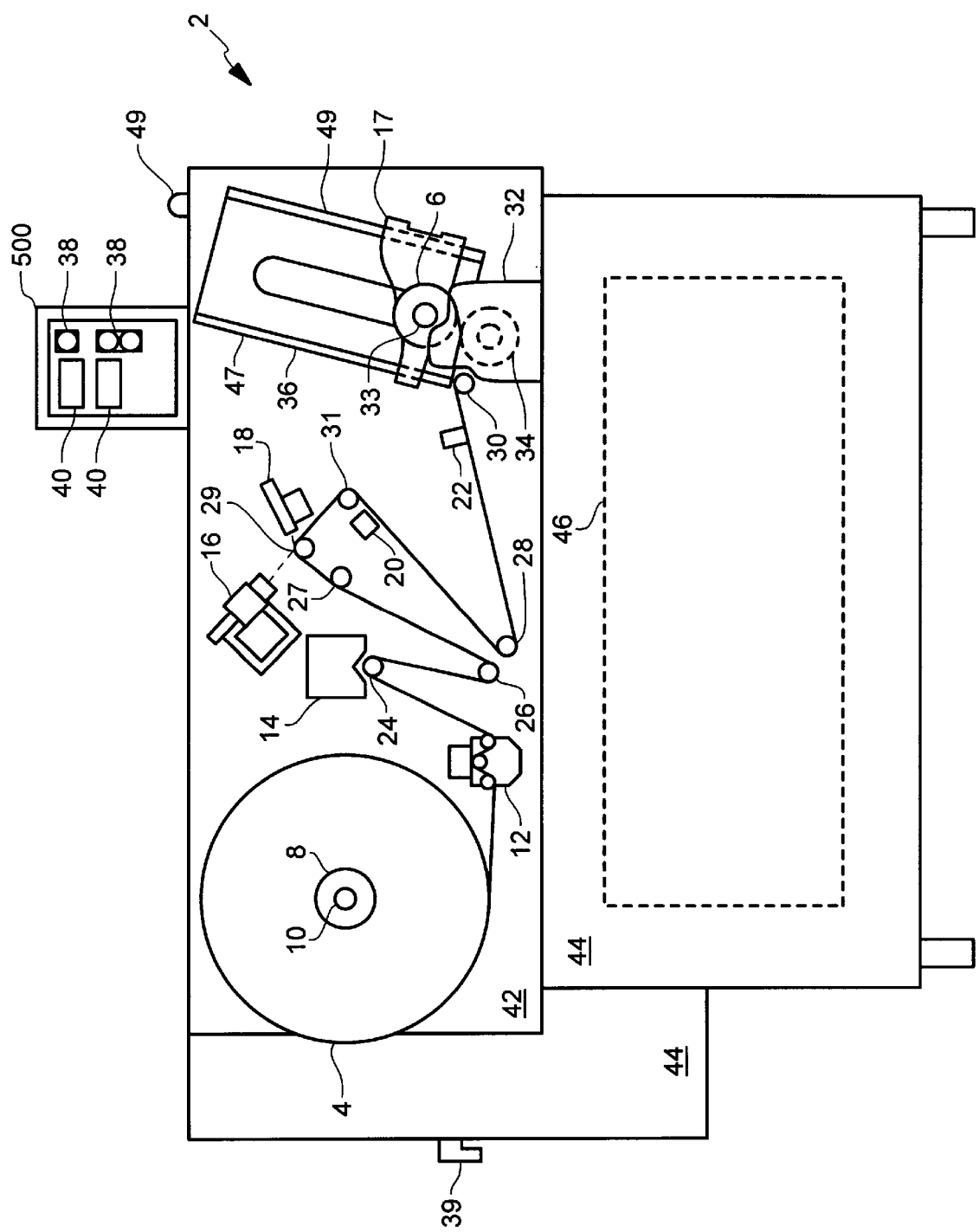
FIG. 3 shows an exemplary rewinder machine according to the present invention when the unwind bobbin is initially loaded.

FIG. 3 shows an exemplary bobbin inspection system 2 according to the present invention. By way of overview, the system 2 includes an unwind spindle assembly (8, 10) for mounting a first bobbin (the unwind bobbin) of paper (or generally, any sheet-like material). The paper from the unwind bobbin 4 is threaded through a tension sensor 12, which, in conjunction with a magnetic particle brake (component 90 in FIG. 5) connected to a shaft of the unwind spindle assembly (8, 10), maintains a prescribed amount of tension on the paper as it is transferred from the unwind bobbin to the rewind bobbin.

From the tension sensor 12, the paper is fed over an idler roller 24 where it is inspected by a photoelectric sensor 14. The photoelectric sensor 14 includes an infrared emitter which projects a beam of infrared radiation onto the paper as it passes over the idler roller 24. The beam is reflected from the paper and received by an infrared detector. Signals received from the infrared detector are conditioned and used to quantify various characteristics of the paper, such as the spacing between bands formed on the paper. As will be discussed, the output of the detector 14 serves as a redundant check of the information provided by the line scan camera 16. From the photoelectric sensor 14, the paper passes over another idler roller 26, and then over a guidepost 27.

From the guidepost 27, the paper is fed over an inspection roller 29 where it is inspected by a line scan camera 16 in conjunction with a light source assembly 18. More specifically, the light source assembly 18 directs light onto the paper as it passes over the inspection roller assembly 29. The light is reflected from the paper and received by the camera 16, which contains a linear CCD array. Information from the CCD array is used to characterize the properties of the paper passing over the inspection roller 29, and thereby supplements the information provided by the photoelectric sensor 14.

After passing over the inspection roller, the paper is fed around another idler roller 31 and then past an ink jet marker assembly 20 which optionally prints information on the passing paper. From there, the paper is passed around yet another idler roller 28 and then past a web break sensor 22 which alerts the system 2 when the paper breaks or the first bobbin 4 has entirely unwound. At this point, the paper is passed over a guidepost 30 and then onto a rewind spindle assembly (6, 33), where it is rewound on a second bobbin core (the rewind bobbin).

Figure 4:
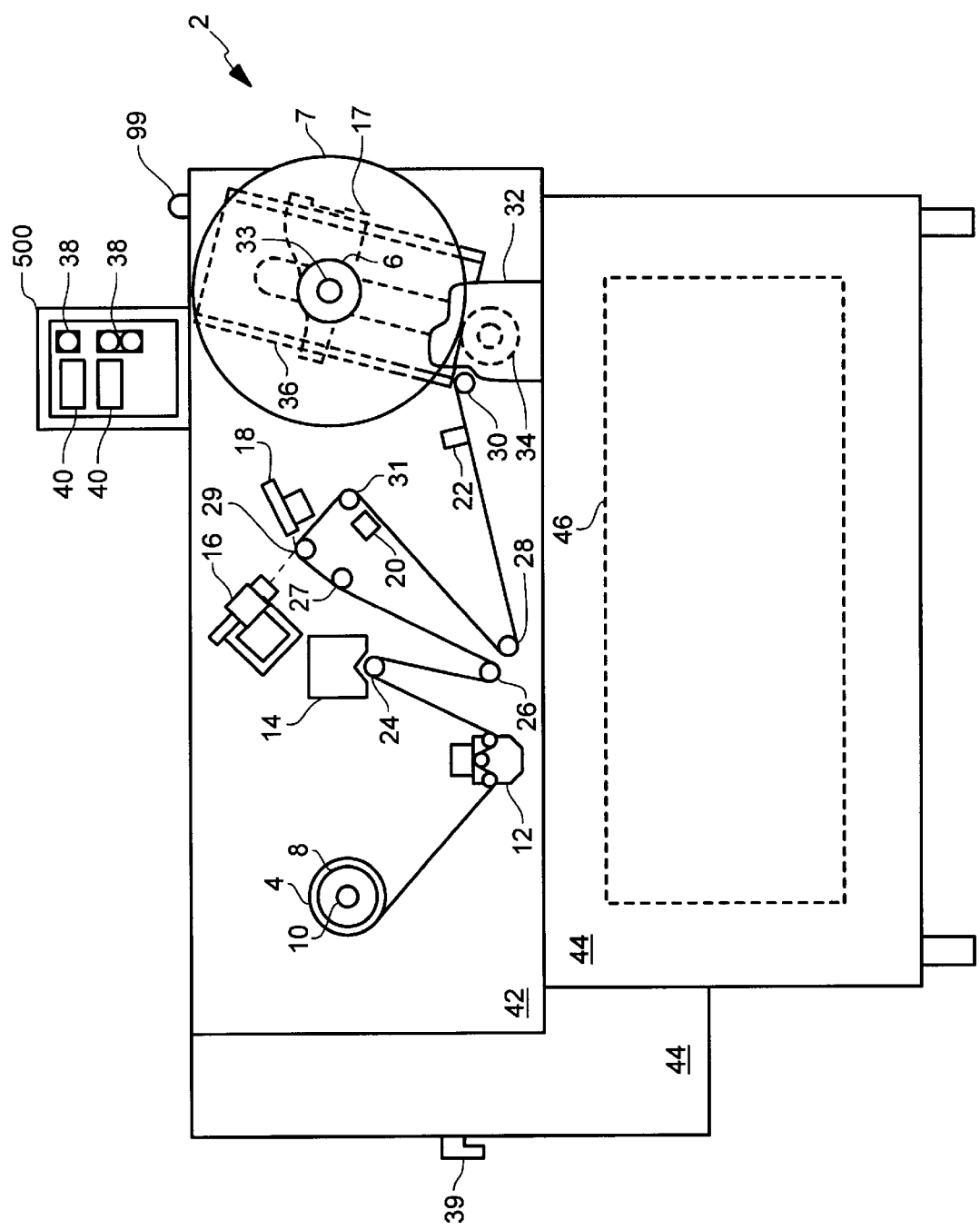
FIG. 4 shows the exemplary rewinder machine of FIG. 3 when the unwind bobbin is almost finished unwinding.
Figure 12:
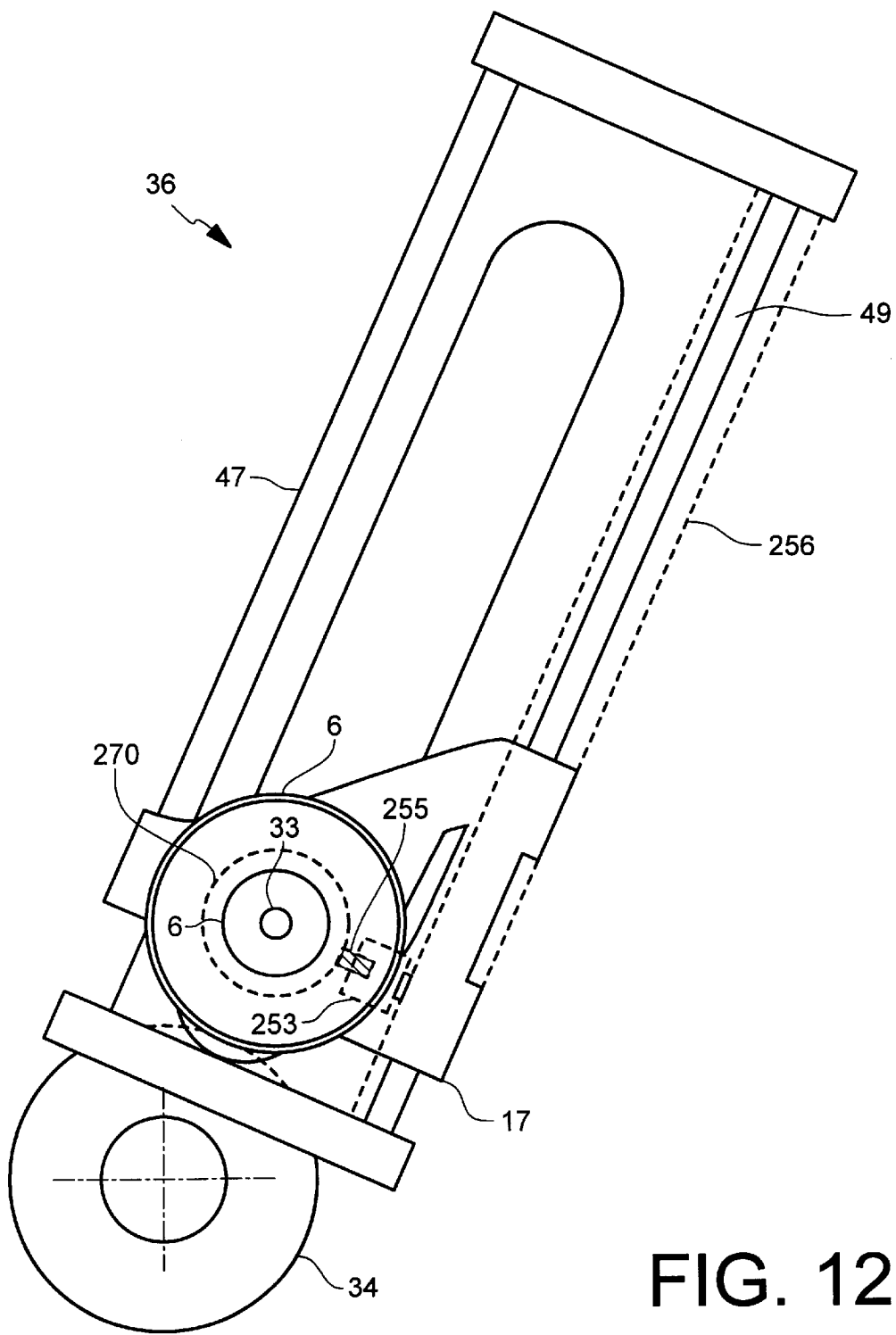
FIGS. 12–13 show a slidable rewinder assembly for use in the rewinder machine of FIG. 3.
Figure 13:
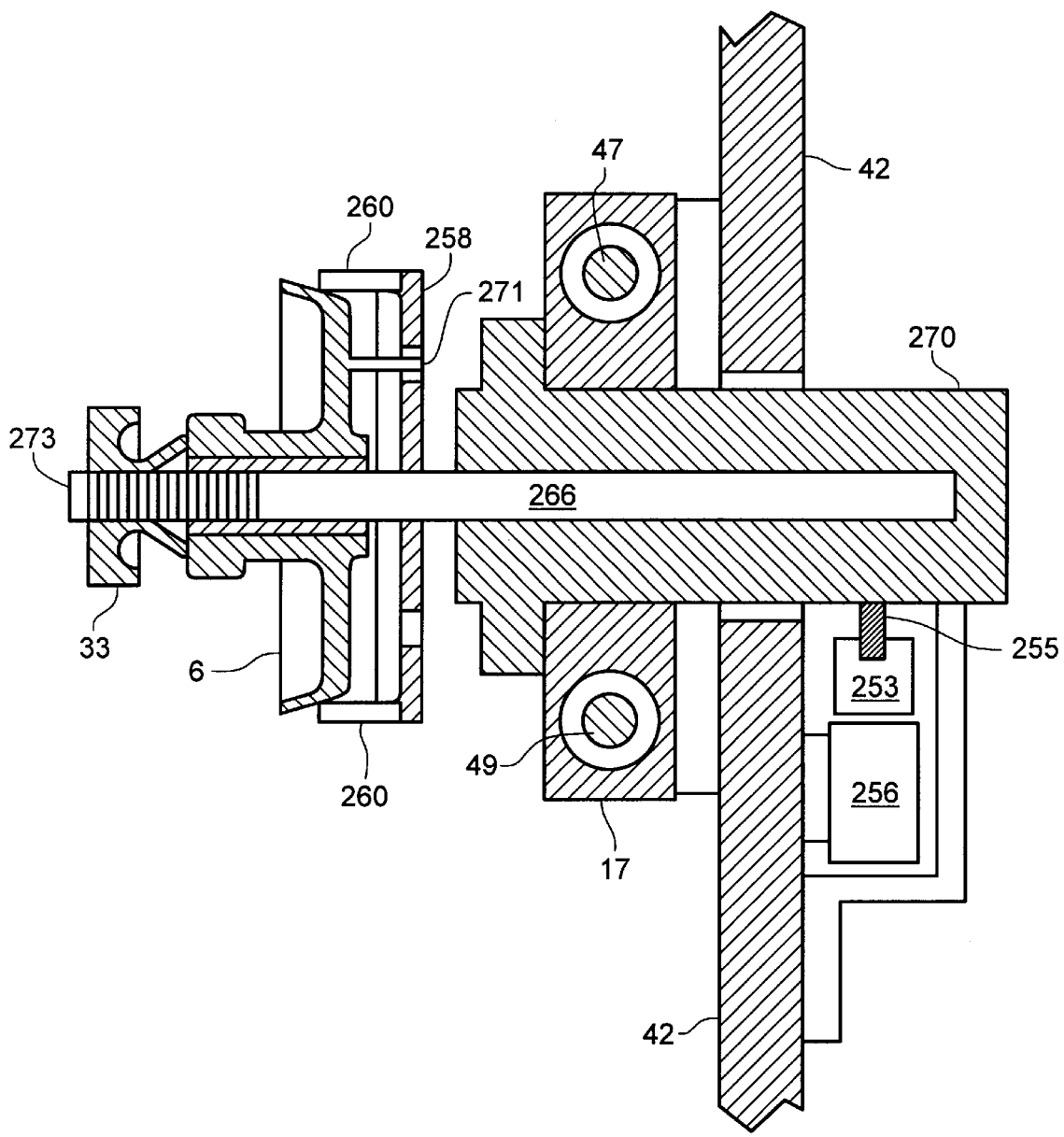

More specifically, the rewind bobbin is pressed firmly against a drive wheel 34 of a drive capstan mechanism by an air cylinder (component 256 in FIGS. 12 and 13). The powered rotation of the drive wheel 34 induces the rotation of the rewind bobbin on the rewind spindle assembly (6, 33) through frictional contact therewith, and thereby rewinds the paper on the rewind bobbin core mounted on the rewind spindle assembly (6, 33). The rewind spindle assembly (6, 33) is mounted to two parallel rails (47, 49) of a "slide" assembly 36 using a mounting member 17. As more paper is wound onto the rewind bobbin core, the mounting member 17 and the rewind spindle assembly (6, 33) slide upward on the slide assembly 36 to accommodate the increasing diameter of the rewind bobbin 7, as illustrated in FIG. 4. The drive capstan will cease rotating the rewind spindle assembly (6, 33) when the web break sensor 22 detects that the end of the paper of the unwind bobbin 4 has been reached. The paper is transferred from the unwind bobbin to the rewind bobbin at high speeds, such as 3000 ft/min.

Figure 14:
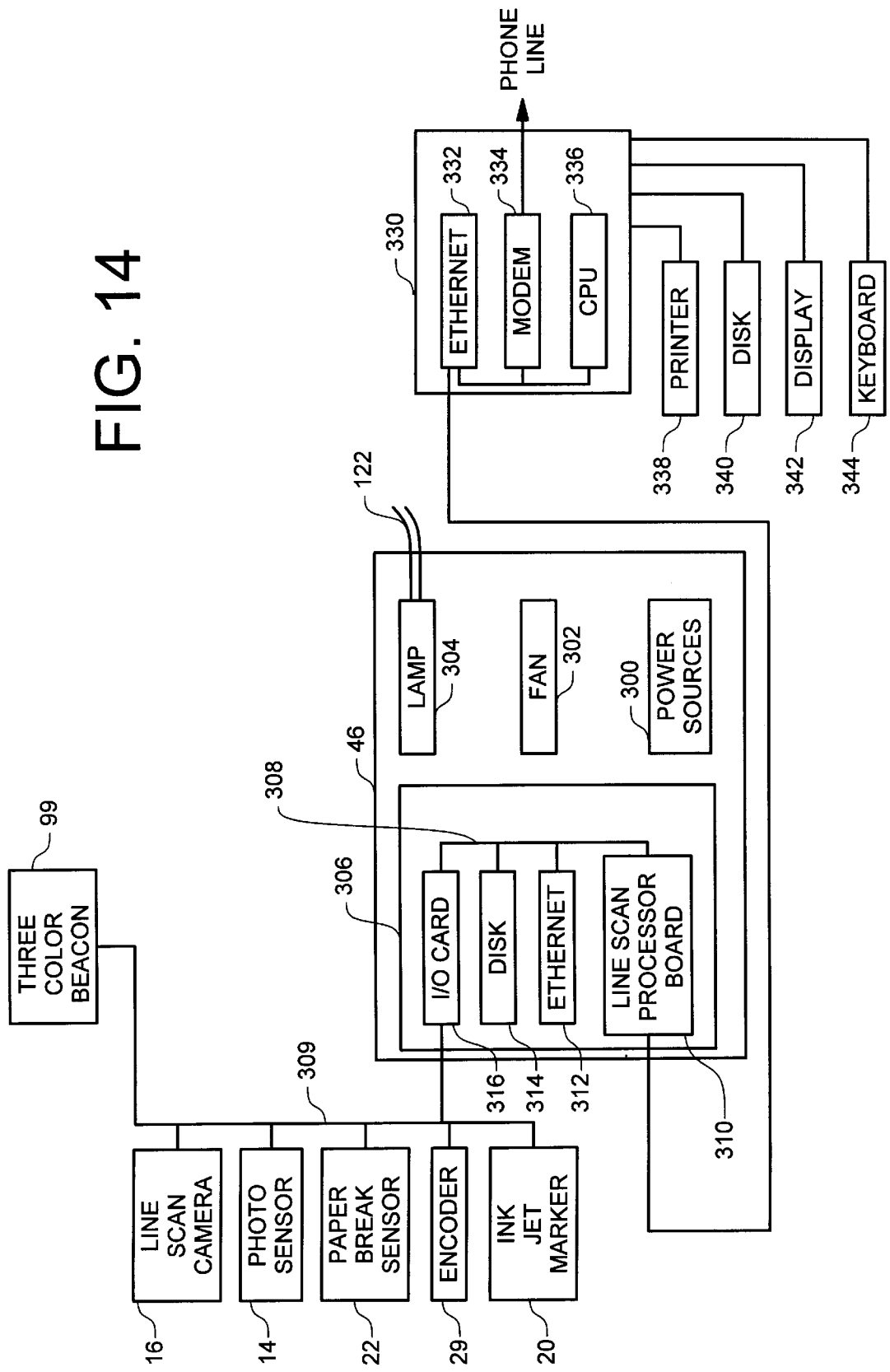
FIG. 14 shows an exemplary electrical/computer configuration for use in the rewinder machine of FIG. 3.
Figure 15:
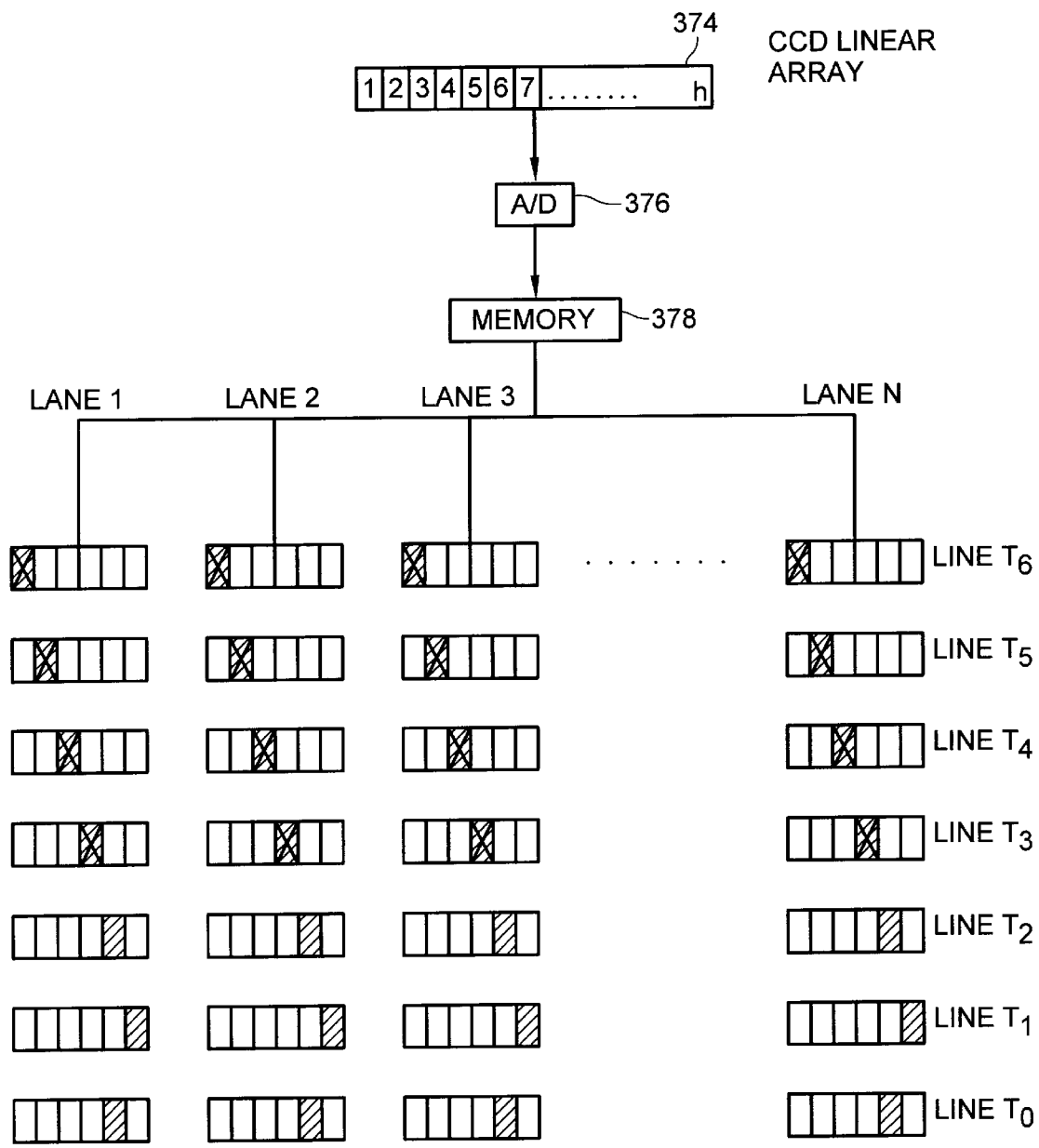
FIG. 15 shows an exemplary technique for processing data from the line scan camera.

The above described components are mounted on a backplate 42, which in turn is supported by a cabinet-like structure 44 (having a left and a right portion, as shown in FIGS. 3 and 4). The cabinet 44 houses much of the processing electronics, power sources and cooling fans (denoted generally as 46) for the system 2. The operator controls the system 2 via a control panel 500, including control inputs (e.g. 38) and monitoring displays (e.g. 40). A 3-color signal beacon 99 presents system status information. Switch 39 turns the power supplied to the inspection system 2 on and off. Additionally, although not shown in FIGS. 3 and 4, the system 2 can be connected to a separate computer workstation via Ethernet connection (e.g. see FIG. 14). Data from the camera 16 can be transferred from the bobbin inspection station 2 to the separate computer workstation for statistical analysis of the characteristics of the paper, and the identification of various anomalies in the paper.

Each of the above described features of the bobbin inspection system will be described in further detail below in connection with FIGS. 5–18.

2. The unwind assembly.

Figure 5:
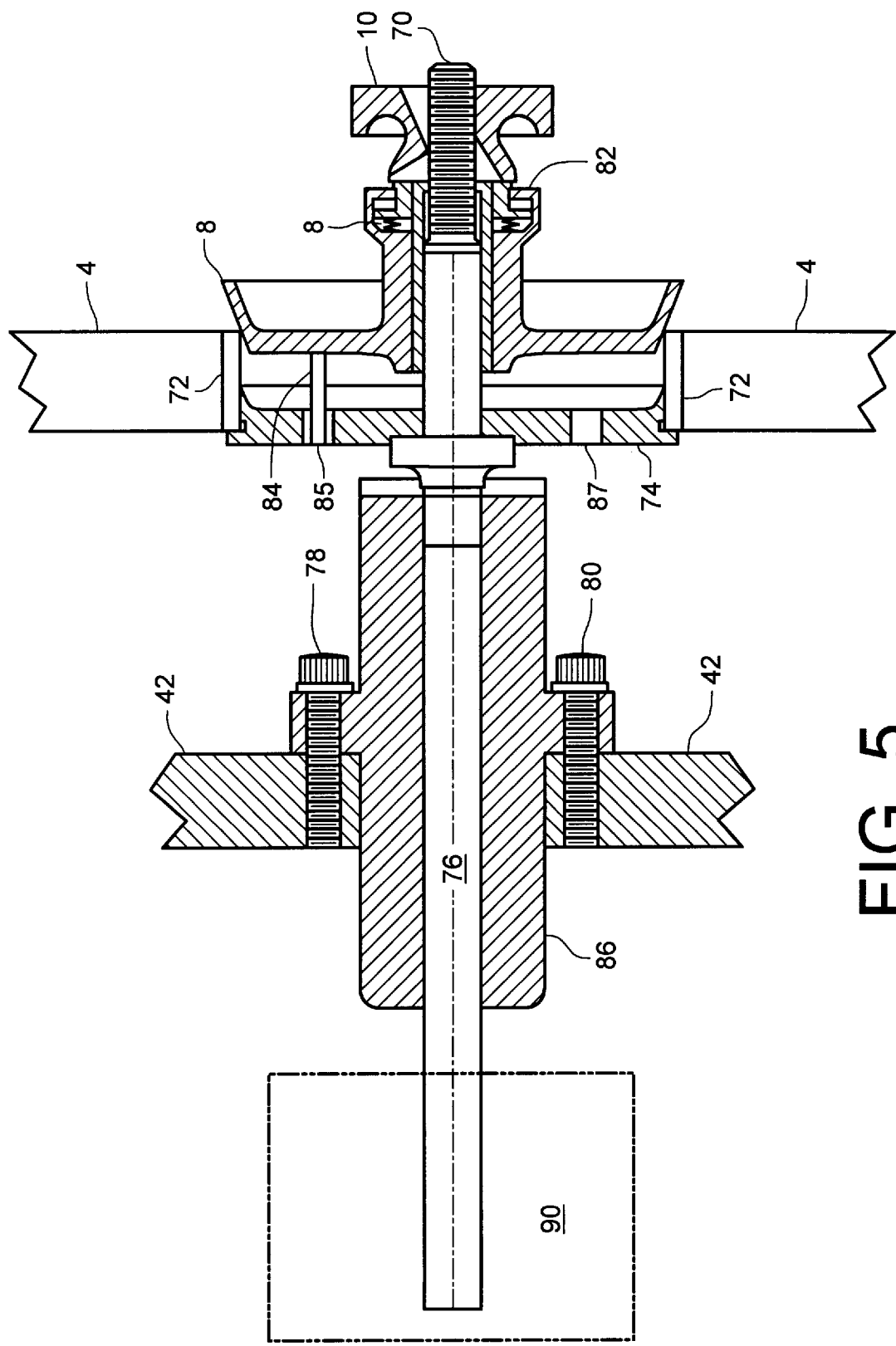
FIG. 5 illustrates an exemplary unwind spindle assembly according to the present invention.

The unwind assembly is shown in FIG. 5. The assembly includes a shaft 76 mounted on ball bearings (not shown) for rotation within a housing 86, which, in turn, is mounted to the backplate 42 by means of bolts 78 and 80. A backing plate 74 is attached to the shaft 76 at one end using one or more screws (not shown). The unwind bobbin 4 is mounted on the backing plate 74. A magnetic particle brake 90 is located on the other end of the shaft 76. The magnetic particle brake 90 exerts resistance on the shaft 76 as its rotates to maintain a prescribed amount of tension on the paper as it is pulled through the inspection system 2. The exact amount of resistance exerted by the particle brake 90 is governed by feedback provided by strain gauge sensor 12 (shown in FIGS. 3 and 4). By way of example, a magnetic brake produced by Magne Corp. (e.g. part no. 5MB90S) can be used as the magnetic brake 90. A tension sensor produced by Cleveland Machine Controls of Cleveland, Ohio (e.g. part no. CMC TSN-A-1) can be used as the strain gauge sensor 12 (shown in FIGS. 3 and 4).

The unwind assembly further includes a cone 8 having a pin 84 which mates with a hole 85 in the backing plate 74. The core 72 of the unwind bobbin 4 is sandwiched between the cone 8 and the backing plate 74. A nut 10 is fastened to the threaded end 70 of the shaft 76 to fix the backing plate 74, cone 8 and unwind bobbin 4 in place relative to each other. The nut 10, in turn, contacts plunger members 82. The plunger members 82 are mounted on springs 83 inside respective cavities in the cone 8.

Figure 6:
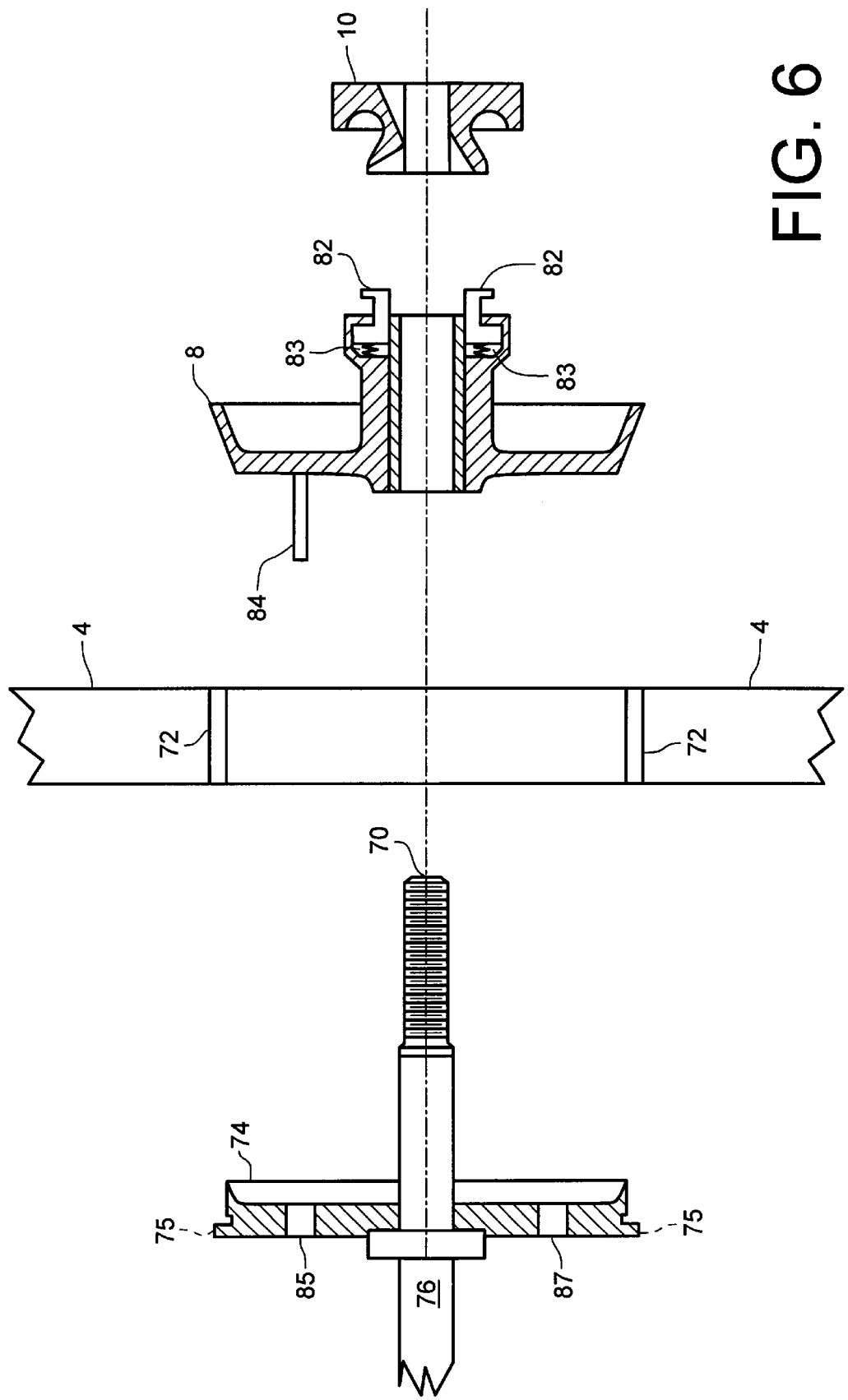
FIG. 6 illustrates an exemplary bobbin clamping mechanism used on the unwind and rewind spindles.

The unwind bobbin 4 is mounted on the backing plate 74 in a manner best shown with reference to FIGS. 6. As shown there, the unwind bobbin 4 is slid over the shaft 76 and onto the backing plate 74. The backing plate has a diameter sized slightly smaller than the inner diameter of the core 72 of the unwind bobbin 4 so that the core 72 of the unwind bobbin 4 slides snugly over the backing plate 74 until it contacts the extended lip 75 of the backing plate.

Once the unwind bobbin is lodged firmly on the backing plate 74, the operator slides cone 8 onto the terminal end of the shaft 76 until it wedges into the core 72 of the unwind bobbin 4. Pin 84 mates with a corresponding hole 85 in the backing plate 74. The pin 84 prevents the cone 8 from rotating relative to the backing plate 74 when the shaft 76 rotates during operation of the inspection station 2. The backing plate 74 includes an additional hole 87 which can mate with the pin 84, instead of the hole 85. Alternatively, the cone 8 can include another pin (not shown) which mates with the hole 87.

Next, the operator secures the bobbin 4 and cone 8 to the backing plate 74 by fastening the quick acting nut 10 onto the threaded end 70 of the drive shaft 76. The nut is designed so that, by orienting the nut at an appropriate angle, it can be quickly slid over the end of the threads of the shaft without engaging the threads. Once the nut contacts the plungers 82 of the cone 8, it can then be angled to engage the threads of the shaft end 70.

The nut 10 applies force on the plunger members 82 as it is tightened on the shaft end 70 (by rotating the nut 10), and thereby compresses the springs 83. The tension provided by the springs 83 prevents the cone 8 from loosening while the machine is running. More specifically, the springs 83, plungers 82 and pin 84 all prevent the unwind bobbin core 72 from slipping relative to the backing plate 74 and cone 8 during the operation of the inspection station 8.

3. The photoelectric sensor.

After mounting the bobbin 4 on the unwind assembly, the paper is threaded through the strain gauge sensor 12 and then over an idler roller 24, where its characteristics are examined by a photoelectric sensor 14.

Figure 7:
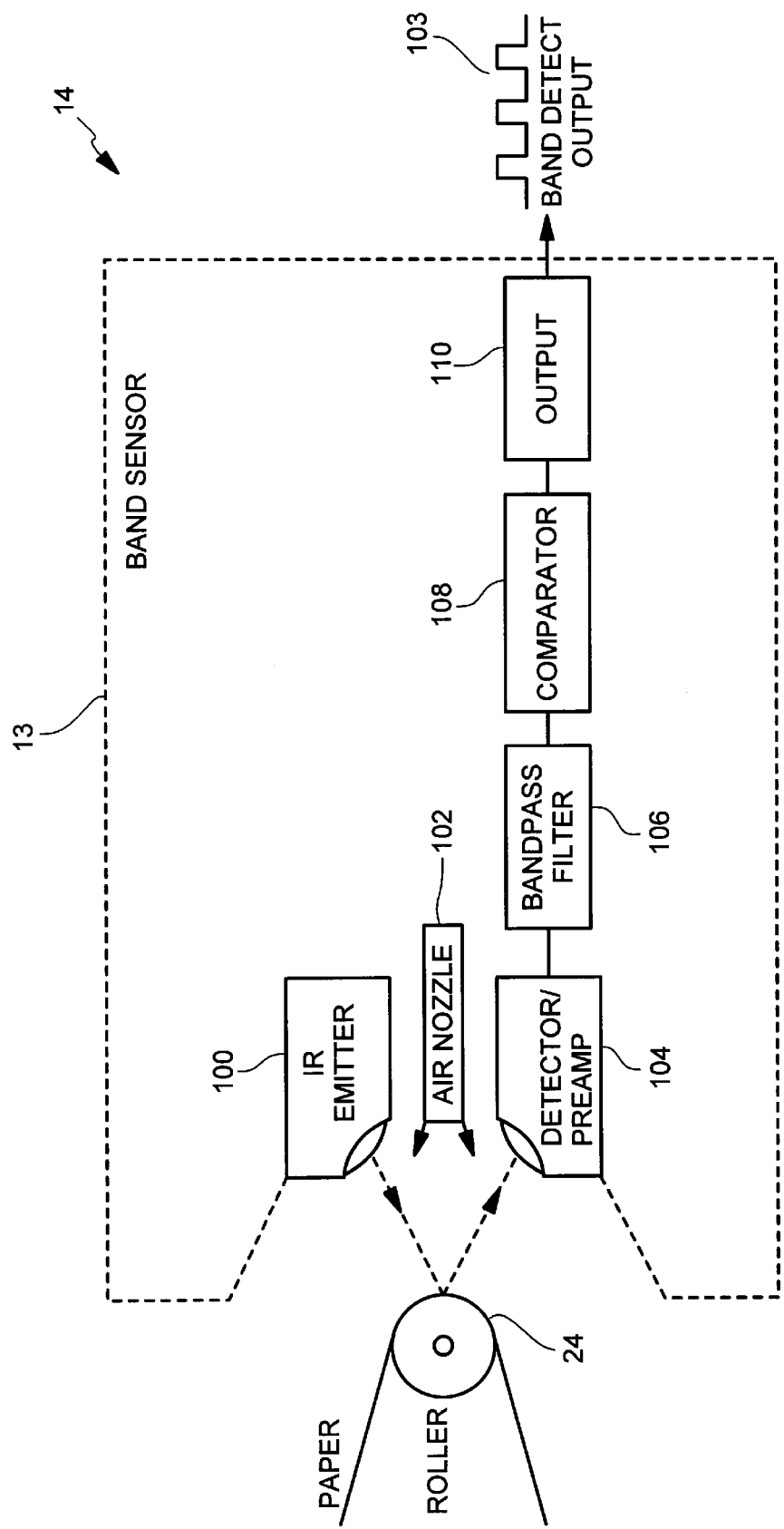
FIG. 7 shows an exemplary photoelectric sensor for use in the rewinder machine of FIG. 3.

FIG. 7 illustrates the exemplary constitution of the photoelectric sensor. As shown there, the system includes an infrared emitter 100 which directs infrared radiation onto the surface of the web as it passes over idler roller 24. The web reflects the infrared radiation. An infrared detector 104 receives and amplifies the reflected radiation. The amplified signal of the detector is filtered to remove extraneous spectral response in filter 106, and then compared with a threshold in comparator 108. Detector responses above the threshold may be indicative of anomalies or bands on the web. A circuit 110 formats the output of the comparator 108. For instance, when the paper contains bands, the output of the circuit 110 produces a pulse train 103. The width of each pulse corresponds to the duration of a band detected by the detector 104.

The above-described components are housed in enclosure 13. An air nozzle 102 provides a stream of air directed at the emitter 100 and the detector 104. The air flow generated by the nozzle 102 blows away dust and other residue which would otherwise degrade the performance of the device.

Further details regarding the photoelectric sensor can be found in commonly assigned U.S. application Ser. No. 08/893,505, filed on the same date as the instant application, which is incorporated herein by reference.

4. The line scan camera and associated components.

Figure 8:
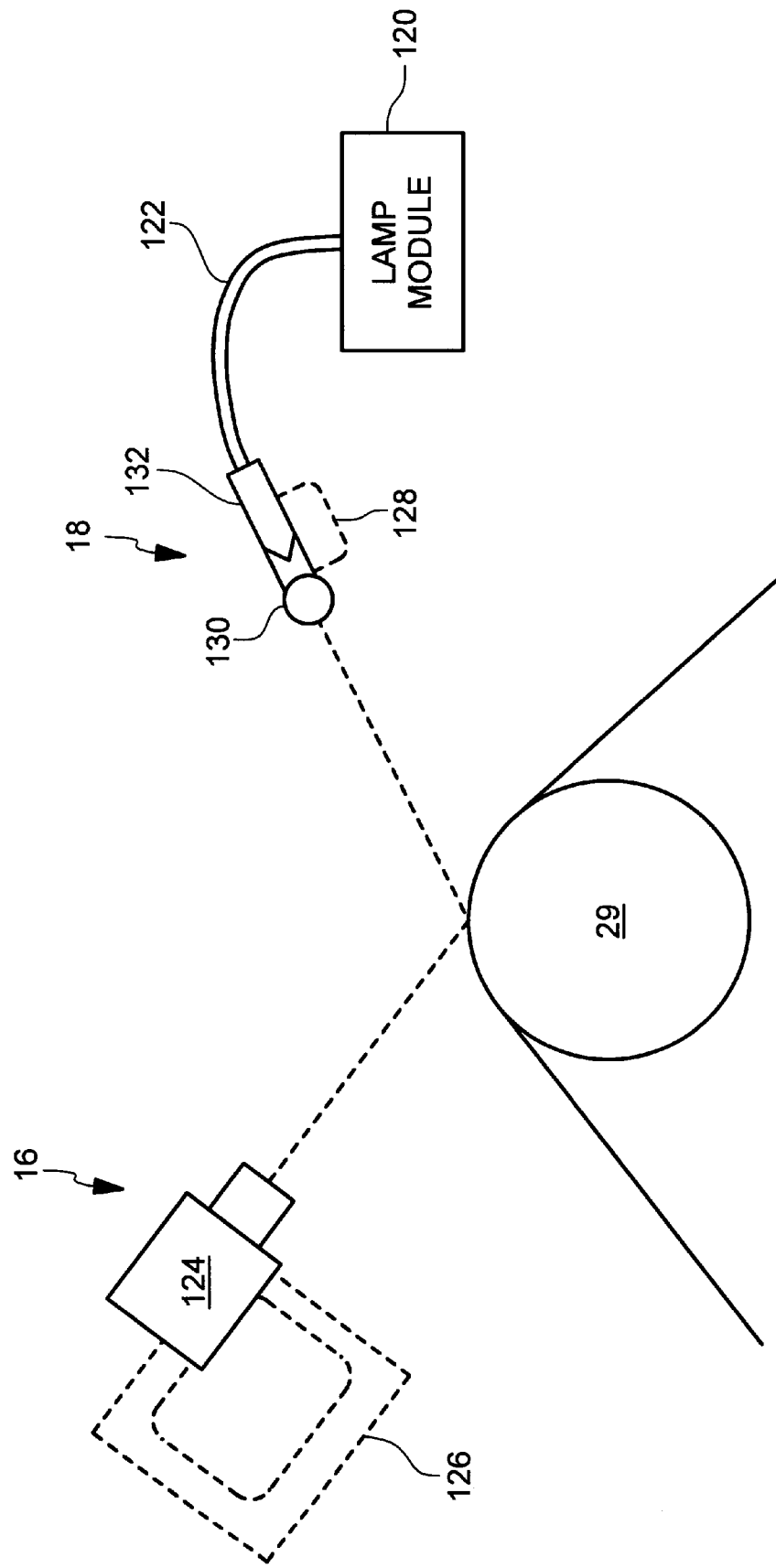
FIG. 8 shows an exemplary line scan camera and associated light distribution assembly according to the present invention.

The camera assembly of the present invention is illustrated in FIG. 8. As shown there, the assembly includes a lamp module 120, such as a 150 watt halogen bulb. The lamp module 120 is preferably located within the cabinet enclosure 44 (shown in FIGS. 3 and 4). The light generated by the lamp module 120 is channeled to a light distribution assembly 18 via a fiberoptic cable 122. The light distribution assembly 18 comprises a light distribution head end 132 for distributing the light laterally across the width of the paper. A rod lens 130 focuses the light from the head end 132 into a narrow stripe of light, which impinges the surface of the paper passing over the inspection roller 29. A bracket mechanism 128 allows the operator to adjust the orientation of the light distribution assembly 18 and thereby alter the angle of the light beam produced thereby.

The light which impinges on the surface of the paper passing over the roller 29 is reflected from the surface of the paper. The reflections are received by a line scan camera assembly 16. The assembly 16 includes the line scan camera 124 supported by positioning bracket 126. The line scan camera 124 includes a linear array of photoreceptive elements (e.g. comprising a 256×1 array or a 1028×1 array). Further details regarding the linear scan camera and light distribution assembly can be found in commonly assigned U.S. application Ser. No. 08/893,538, filed on the same date as the instant application, which is incorporated herein by reference.

FIGS. 9 and 10 illustrate the inspection roller 29 in more detail. As shown there, the inspection roller 29 includes a rotating cylinder 162 (e.g. containing ball bearings which are not shown) attached to a stationary member 160. The stationary member 160 is, in turn, connected to the back plate 42 by means of bolt 158. The end of the inspection roller 29 includes grooves 152 arranged at regular intervals around the periphery thereof. The line scan camera 124 senses these grooves and the rate at which they move. The rate provides a time base from which the system calculates parameters such as band width and the spacing between bands; in this context, the inspection roller 29 and the camera 124 serve as an encoder.

Those skilled in the art will recognize that other types of encoders can be used to provide the common frame of reference. For instance, a proximity sensor can be used to detect the rate at which a pulse wheel rotates (where the pulse wheel is mounted to a rotating member of the inspection station 2). A tachometer can also be used as the encoder.

The output of the encoder is also used as a common frame of reference to synchronize various activities in the system. For instance, the encoder can be used to calculate the speed of the paper, which, in turn, allows the ink jet printer 20 (with reference to FIG. 3) to mark the location of irregular bands detected "upstream" by the camera assembly 16. More specifically, when the camera assembly 16 detects an irregular band, a timer is initiated having an initial time value equivalent to the amount of time it takes a portion of the paper to move from the camera assembly 16 to the ink jet printer 20. When the timer counts down, the ink jet printer 16 prints a mark on the paper at the location of the irregular band. This feature is particularly advantageous because it allows the operator to revisit the location of anomalies sensed by the camera (and/or the sensor 14) and further analyze these anomalies. Alternatively, the ink jet printer can be disabled if the operator does not want to inspect the irregular portions of the paper.

5. The drive capstan and rewind assembly.

Figure 11:
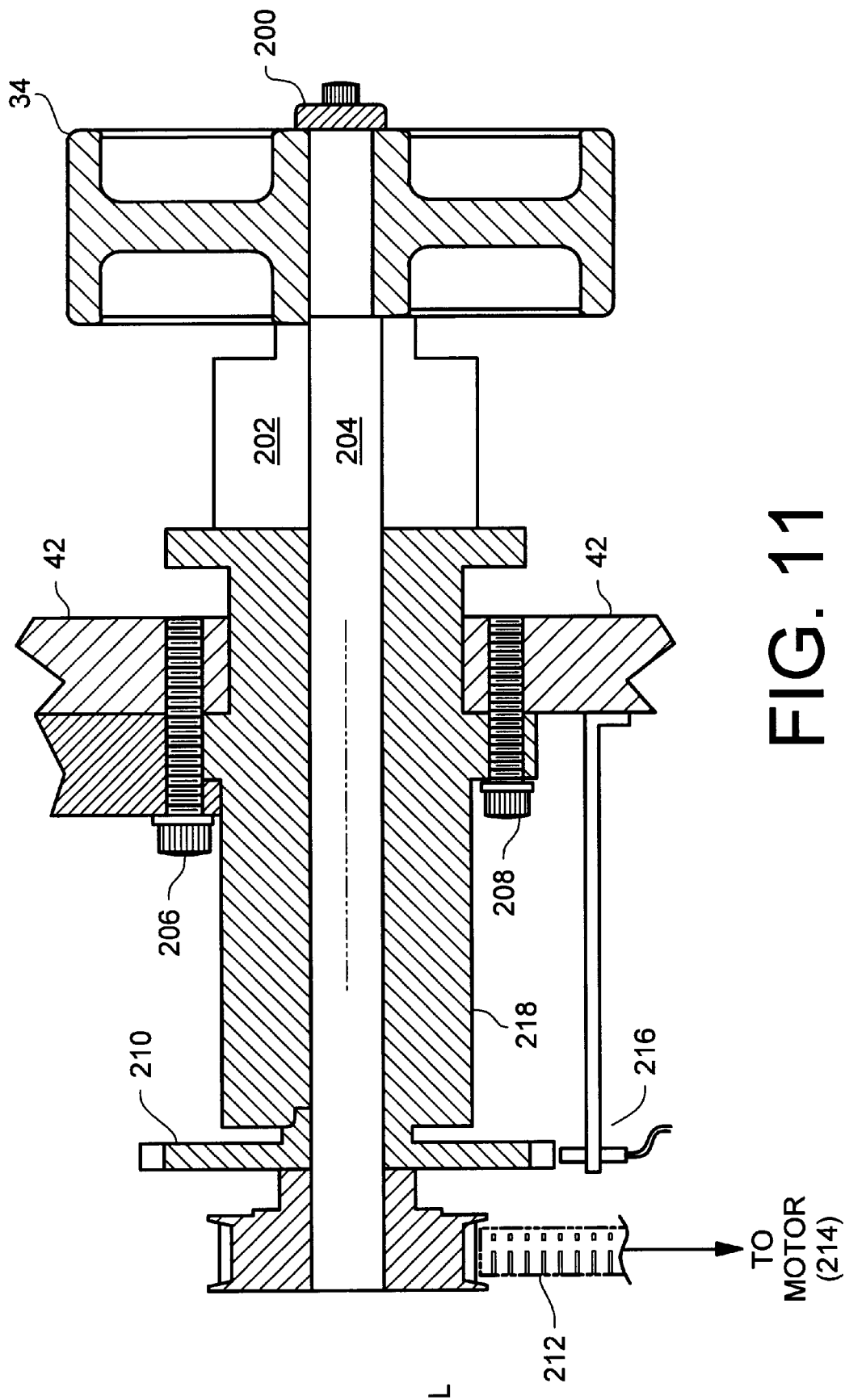
FIG. 11 shows a capstan mechanism for powering the rewind assembly for use in the rewinder machine of FIG. 3.

The drive capstan is illustrated in FIG. 11. The drive capstan includes a drive wheel 34 secured to a rotating shaft 204 (including ball bearings which are not shown) by fastening element 200. The shaft 204 is connected to a pulley and timing belt 212 at its opposite end. A motor 214 (not shown) rotates the shaft 204 by means of pulley 212, and thereby rotates the drive wheel 34. The speed at which the shaft 204 is rotated is governed by feedback provided by pulse wheel 210 in conjunction with a proximity sensor 216, as will be readily understood by those skilled in the art. Furthermore, an electromagnetic brake device 202 halts the rotation of shaft 204 upon detecting a paper break signal from the sensor 22. Mechanically, the shaft 204 rotates in supporting structure 218, which is secured to the back plate 42 using bolts 206 and 208.

Returning to FIG. 4, when a rewind bobbin 7 is loaded on the rewind spindle (6, 33), the outer surface of the rewind bobbin 7 is pressed against the drive wheel 34. As such, the rotation of the drive wheel 34 causes rewind bobbin 7 to rotate, and thereby rewinds the paper onto the rewind bobbin 7.

FIG. 12 shows the rewind assembly in greater detail. As illustrated there, the rewind spindle assembly (e.g. 6, 33) is attached to a mounting member 17, which itself is attached to two rods (47, 49) of a slider assembly 36. As the winding process advances, the diameter of the rewind bobbin 7 increases, causing the mounting assembly 17 and the attached rewind spindle assembly (e.g. 6, 33) to slide upward on the rods (47, 49).

FIGS. 13 shows a cross section of the rewind assembly of FIG. 12. With reference to FIGS. 13, the rewind spindle assembly includes many of the same components as the unwind spindle assembly discussed with reference to FIGS. 4 and 5. The unwind spindle includes a backing plate 258, a cone 6 having a pin 271, and a nut 33 which engages the threaded end 273 of a shaft 266. The shaft 266 is supported by housing 270. The housing 270, in turn, is connected to mounting member 17 which moves up and down on rods (47, 49).

With reference to both FIGS. 12 and 13, the rewind assembly includes an air cylinder 256 behind the backplate 42. The air cylinder 256 is connected to member 253, which in turn is connected to the housing member 270 via pin 255. In operation, the air cylinder 256 moves member 253 either up or down, and thereby moves the attached housing 270 and rewind bobbin 7 up and down. While the inspection system 2 is rewinding, the air cylinder 256 applies downward force on the rewind spindle (6, 33), which firmly presses the rewind bobbin 7 against the drive wheel 34. This ensures that there is a good frictional contact between the rewind bobbin 7 and the drive wheel 34, and allows the system to evenly and cleanly rewind the paper on the rewind bobbin 7.

6. The electrical and data processing components.

The majority of the electrical infrastructure of the inspection machine is located in the cabinet enclosure 44. A more detailed illustration of the components of the cabinet enclosure can be found in FIG. 14.

As shown there, the cabinet enclosure 44 includes a computer processing module 306 which includes an I/O card 316, a flash disk 314, and Ethernet interface 312 and one or more line scan processor boards 310, all of which are connected together on an internal bus 308. Additionally, the cabinet enclosure 44 contains a lamp module 304 for supplying light via fiber optic cable 122 to the light distribution element 18. To cool the components, the enclosure includes one or more fans 302. Finally, the enclosure 44 includes one or more power sources 300 for supplying appropriate power supplies to the components of the machine.

The processing module 306 of the rewinder machine interacts with various components of the rewinder machine, including the three color beacon 99, line scan camera 16, photosensor 14, paper break sensor 22, encoder 29, and ink jet marker 20. These components can be connected to the processing module 306 via their own dedicated lines (not shown) or a common control bus 309. Other components of the machine not shown in FIG. 14, such as the strain gauge 12, magnetic particle brake 90, motor 214, proximity sensor 216 and electromagnetic brake 202 are not directly connected to the computer processing module 306, but are rather controlled via the control panel 36 in a manner which will be readily apparent to those skilled in the art.

The Ethernet interface 312 of the processing module 306 provides connection to an Ethernet interface 332 of workstation 330. The workstation 330 includes a modem 334 for transferring information to a remote computer (not shown) over a phone line, and a controlling CPU 336. The workstation has associated therewith the following peripheries: printer 338, disk 340, display 342, and keyboard 344.

7. Application of the rewinder for band inspection.

The rewinder machine discussed above has many applications. The rewinder is especially well adapted to detecting anomalies in cigarette paper having bands, as will be discussed at length as follows.

Figure 1:
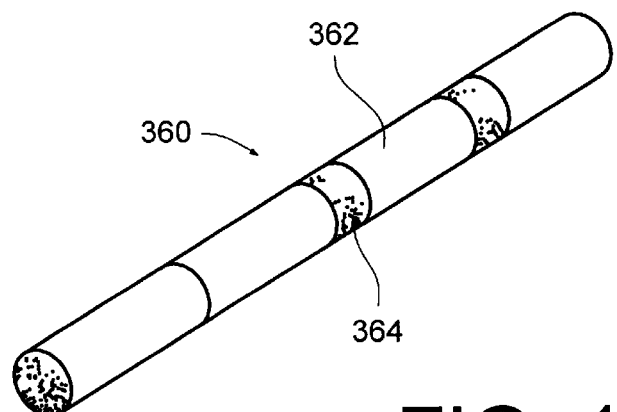
FIG. 1 shows an exemplary cigarette containing banded regions.

Commonly assigned U.S. Pat. Nos. 5,417,228 and 5,474,095 disclose cigarette papers comprising a base web and banded regions of add-on material. For instance, returning to FIG. 1, an exemplary cigarette 360 contains two bands 364 formed by depositing a layer of pulp on base cigarette paper 362. Cellulon, microcrystalline cellulose, flax or wood pulp, or amylopectin are some of the various preferred substances which have been used to form the bands.

Commonly assigned U.S. Pat. No. 5,534,114 discloses that the above described bands can be formed by modifying a conventional Fourdrinier paper making machine to deposit additional layers of cellulose at some stage in the production of the cigarette base paper 362. To streamline the process, the bands are preferably applied while the paper is moving at high speeds, such as 500 feet per minute. At these high speeds, breakdowns and other factors (such as clogged band applicators), can result in the production of irregular bands.

Figure 2:
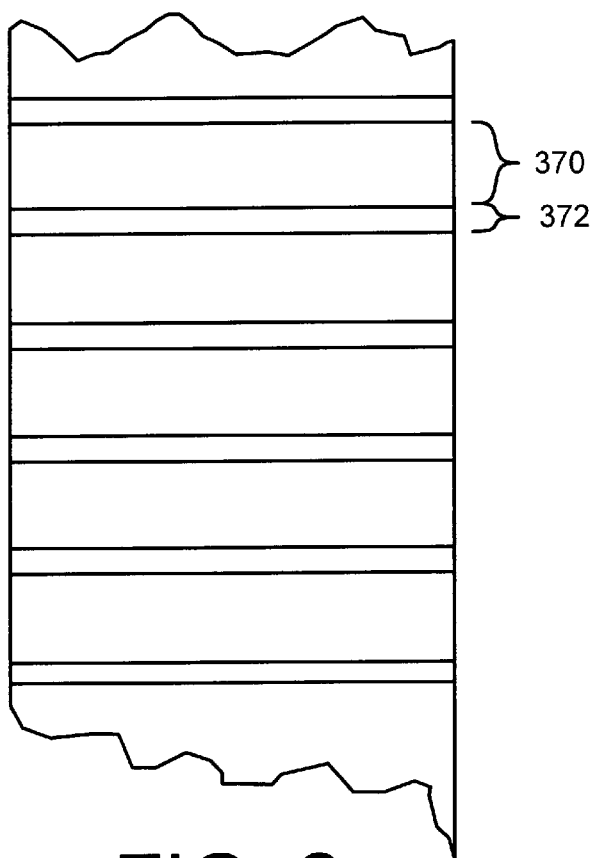
FIG. 2 shows an exemplary web of cigarette material including bands.

For example, as illustrated in FIG. 2, common irregularities arise when the width of a band 372 deviates from a desired width, or the band becomes skewed so that it is no longer orthogonal with respect to the edge of the paper. Other irregularities arise when the separation between two bands (e.g. 370) deviates from a desired separation width. Moreover, a given band applicator can produce a band with gaps or a band having a contrast which is either too high or too low. The present invention, using the line scan camera 16, can be employed for monitoring the band width, band spacing and band contrast.

More specifically, the camera 16 can employ a 256×1 CCD array (element 374 with reference to FIG. 15) which receives reflections which span the lateral dimension of the web passing over the inspection roller 29. The exemplary resolution of the array in the lateral direction across the roller 29 is 0.2 mm. Furthermore, the CCD array is exposed at a rate which allows the computer to sample information at a resolution of 0.2 mm in the longitudinal direction. Thus, the array effectively samples elements having a spatial dimension on the paper of 0.2 mm×0.2 mm. Accordingly, each element of the CCD array includes a value indicative of the magnitude of the reflection sensed in a 0.2 mm×0.2 mm portion of the moving web.

The data from the linear array is thereafter converted from analog to digital form in A/D converter 376 and stored in memory 378 of one of the scan processor boards 310. The processor 306 then divides the data from each array into a series of contiguous lanes (e.g. a total of 32 lanes in one embodiment). To facilitate discussion, each lane shown in FIG. 15 comprises 6 contiguous pixel elements, although each lane will typically include many more pixels. The magnitude of each pixel is quantified into one of 255 different levels.

During each exposure, a single pixel from each lane is compared with a dynamic threshold. Pixels above the given threshold are indicative of banded regions of the web, while pixels below the given threshold are marked as non-banded regions. Upon the next exposure, the next contiguous pixel in the lane is exposed, and the comparison is repeated. For example, at an arbitrary time denoted $t_0$, the fifth pixel in each lane is compared with the dynamic threshold (e.g. see bottom-most row of lanes denoted as "line $t_0$"). In the next exposure, the sixth element is compared to the threshold (e.g. see the rows of lanes denoted as "line $t_1$"). After this, the system will continue back in the opposite direction, choosing the fifth pixel for comparison with the threshold in line $t_2$. Thus, the pixel chosen for comparison with the threshold varies in a serpentine path, as generally denoted by FIG. 15. According to another embodiment, the inspected pixel is not advanced at each line. Rather, in this embodiment, the processing module dwells on each pixel for a prescribed number of lines (e.g. corresponding to 30 mm), after which it will advance to a next adjacent pixel. The comparison of only one pixel out of each lane enhances processing speed without significantly degrading performance.

The pixel elements marked with an "X" denote a pixel value above the dynamic threshold. Thus, it is seen that a band started at line $t_3$.

Figure 16:
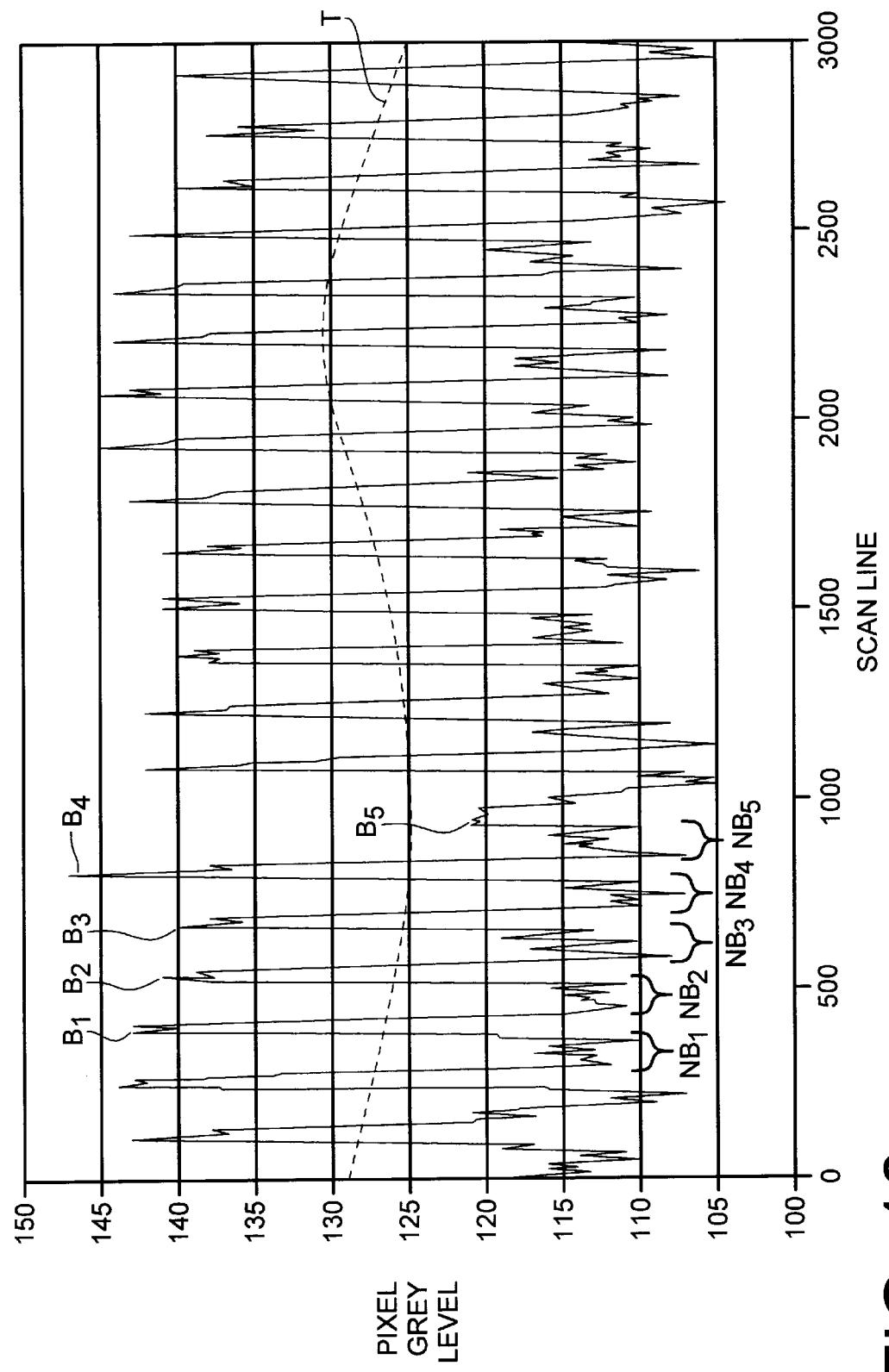
FIG. 16 illustrates how the present invention alters the band detection threshold (T) to compensate for the changing baseline of the image.

The threshold used to detect a band region and a non-band region is dynamic in the sense that it varies to accommodate changes in the base paper, band material, or measuring environment. For instance, as shown in FIG. 16, an exemplary waveform of pixel gray level as a function of scan line shows local perturbations which represent transitions from background non-banded regions (e.g. as in regions $NB_1$, $NB_2$, $NB_3$, $NB_4$ and $NB_5$) to banded regions (e.g. as in regions $B_1$, $B_2$, $B_3$, $B_4$ and $B_5$). The waveform also shows a global change in which the general baseline of these local perturbations slowly undulates. For example, the global undulation is at its lowest point around the scan line 1000, and at its highest point around scan line 2000. This global undulation is primarily due to changes in the basis weight of paper caused by uneven application of pulp by the paper making machine. The present invention takes this phenomenon into account by adjusting the threshold level (T) so that it generally tracks the changing baseline of the waveform.

One technique for dynamically varying the threshold level is described as follows. Generally, the threshold at any given moment is a function of the gray levels of the immediately preceding band region or regions, and the gray levels of the immediately preceding non-band region or regions. In one embodiment, the threshold represents a moving average of previous non-band background (e.g. an average of $NB_1$, $NB_2$, etc.) plus the greater of (1) a set constant (such as 10 gray levels), or (2) 50% of the moving average of peak heights of the banded regions (e.g. an average of the heights of $B_1$, $B_2$, etc.). For example, consider the band region $B_3$. The threshold used to discriminate this band region is determined by first calculating the average background level of the non-band regions $NB_2$ and $NB_3$. Thereafter, an average peak height value is determined by computing the average of the heights of the $B_1$ and $B_2$ band regions. The "height" of a band region generally corresponds to the difference in pixel gray level between the band region and a subsequent non-band region. In making this measurement, a single gray level can be used to represent the gray level of the band region (such as the maximum gray level), or an average of gray levels within the band region can be used. Similarly, a single gray level can be used to represent the gray level of a subsequent non-banded region, or an average of gray levels within the subsequent non-banded region can be used. After computing the peak heights in this manner, half of the average peak heights (e.g. from $B_1$ and $B_2$) is compared with the preset value. The greater of the two is added to the average background level (computed above) to derive the threshold value. For example, the average of the heights of $B_1$ and $B_2$ is approximately 30 gray levels, half of which is 15 gray levels. If the preset value is set at 10 gray level values, then the algorithm will select 15 as the value to be added to the average background. However, if a series of shorter peaks (such as $B_5$) are encountered, then the algorithm will rely on the preset value (e.g. of 10 gray levels) to discriminate band regions from non-band regions. The preset value is preferably set at least high enough so that noise in the non-banded region will not be misinterpreted as the start of a band region.

It will be readily apparent to those skilled in the art that the window selected for calculating the moving average of peak heights and non-banded region levels need not be restricted to two banded regions and two non-banded regions, respectively. A smoother threshold can be obtained by widening the window. Furthermore, the above discussed threshold levels are dependent on the type of paper and the band material used, as well as the operating environment; the specific values cited above are entirely exemplary.

Figure 17:
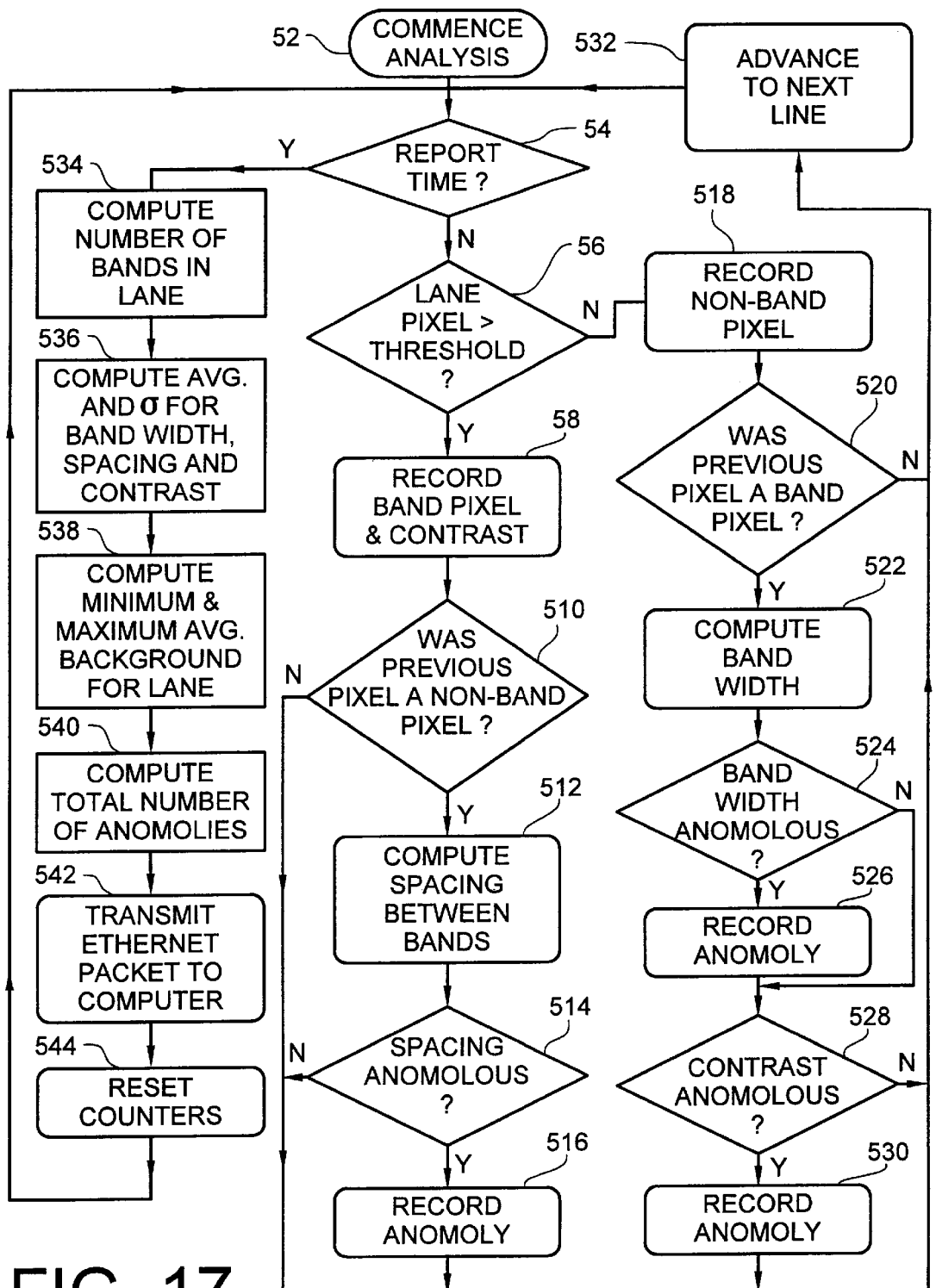
FIG. 17 shows an exemplary algorithm for determining various properties of the bands imaged by the line scan camera.

The actual task of determining the characteristics of the bands can be understood with reference to the flowchart shown in FIG. 17. The analysis commences at step S2, followed by a determination whether it is time to report data from the processing board 310 to the workstation 330 over the Ethernet network (step S4). In an exemplary embodiment, the processing performed by board 310 is reported every half second (or every 1/10 of a second for more timely reporting). Having just commenced analysis, the results of this query will be answered in the negative, and the system will advance to step S6. In step S6 it is ascertained whether the pixel in a lane is above the dynamic threshold. To facilitate discussion, step S6 is framed in the context of a single lane. However, it should be kept in mind that the output of each array is divided into a plurality of lanes. Thus the comparison shown in step S6 is in actuality repeated many times for different lanes. Preferably the processing board 310 performs the computations for different lanes in parallel to improve processing speed.

If it is determined in step S6 that the magnitude of the pixel is above a dynamic threshold, then the algorithm advances to step S8, where the presence of a banded pixel and its contrast are recorded. If the previous pixel in the previous line was not a band pixel (as determined in step S10), then the current line represents a start of a band. This would correspond to line $t_3$ shown in FIG. 15, since the previous line at $t_2$ contained a pixel below the dynamic threshold. It is therefore possible at this time to determine whether the spacing between the present band and the last encountered band (if appropriate) is within prescribed tolerances (steps S12 and S14). If the band spacing is either too long or too short, this fact is logged in step S16, whereupon the algorithm advances to the next line in step S32.

If, on the other hand, the pixel examined in step S6 is below the dynamic threshold, then this fact is recorded in step S18. It is then determined if the previous examined pixel in the previous line was a band pixel (step S20). If so, this marks the end of a band, and it is then possible to determine the average contrast of the band and the width of the band (step S22). It is determined whether these values are outside of prescribed tolerances (steps S24–S30). If so, these anomalies are recorded and the algorithm advances to the next line in step S32.

Supposing, at this time, it is determined that a half of a second has elapsed (in step S4). This causes the line scan processor 310 to enter its report mode. As shown in FIG. 17, the processor 310 will compute the number of bands in the lane over the last half of a second (step S34), the average and standard deviation for band width, band spacing and band contrast (step S36), the minimum and maximum average background for the lane (step S40) and the total number of anomalies (e.g. out of tolerance band width, spacing and contrast) (step S40). This information is assembled into a packet which is forwarded to the workstation 330, and then the various counters used to compute the totals are reset (in step S44).

Figure 18A:
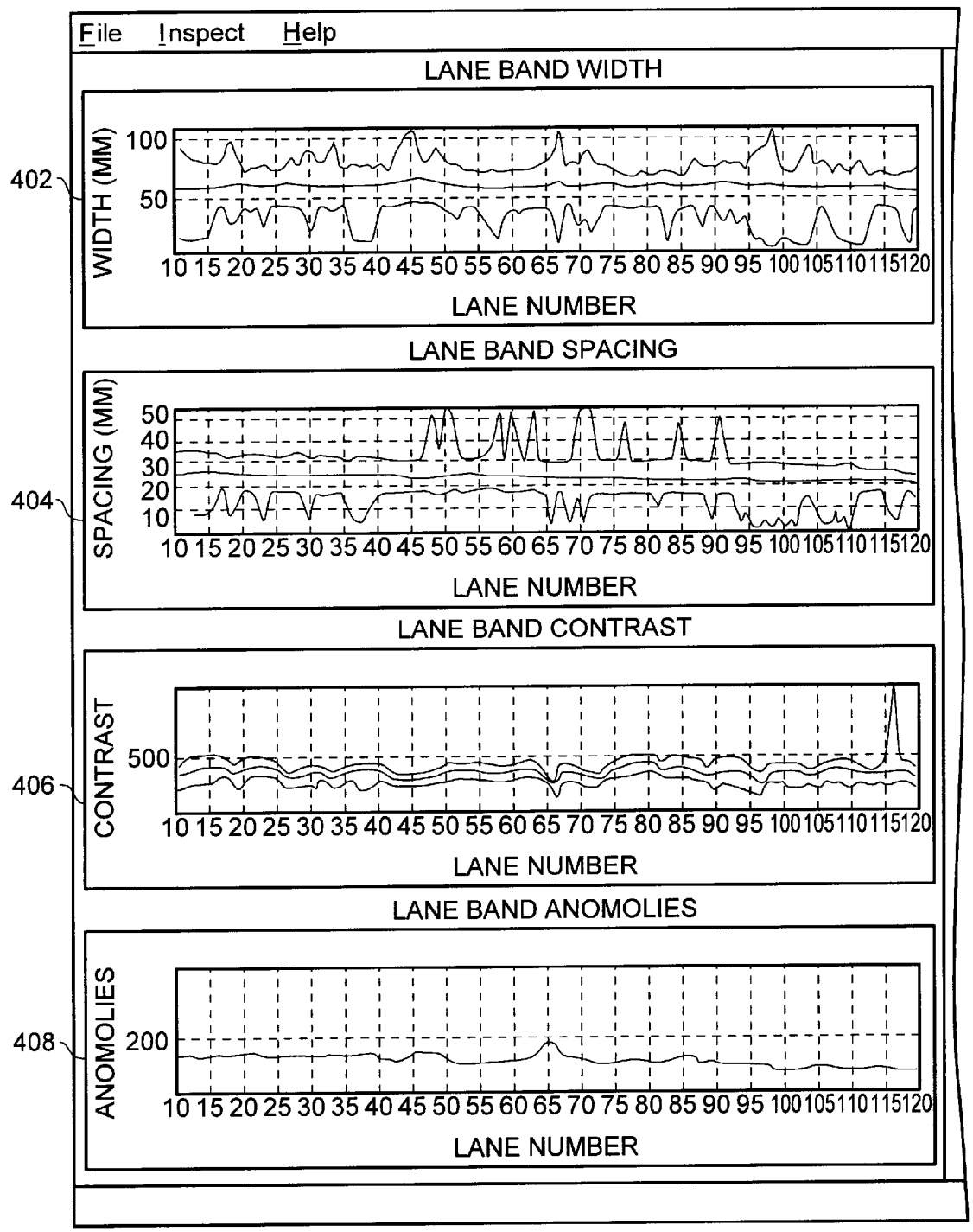
FIG. 18 shows an exemplary statistical display of various properties of the bands imaged by the line scan camera.

The workstation 330 then aggregates this information with previously transmitted information to provide a statistical summary of the quality of the bobbin paper. This information is displayed on display panel 400 as illustrated in FIG. 18. The panel 400 includes a first subpanel 402 listing the band width as a function of lane number for the last reporting interval. A subpanel 404 illustrates band spacing as a function of lane number for the last reporting interval. A subpanel 406 illustrates band contrast as a function of lane number of the last reporting interval. Finally, subpanel 408 illustrates the number of band anomalies (aggregate of band spacing, band width, and contrast anomalies) as a function of lane number for the last reporting interval. The subpanels 402, 404 and 406 contain a middle line indicating the average values of the band width, band spacing and band contrast over the half second interval of reporting. The two other curves bracketing the middle curves denote the plus and minus $3\sigma$ readings. The middle curve can be shown in green, while the $3\sigma$ curves are shown in red so that they can be more readily distinguished.

In addition to the current lane summary, the workstation 330 provides statistics summarizing the characteristics of the unwind bobbin since the start of operation of the rewind machine. Notably, subpanel 410 illustrates the composite band width (e.g. the average bandwidth) as a function of time. Subpanel 412 illustrates composite band spacing 412 as a function of time. And finally, subpanel 414 shows composite band contrast as a function of time. Thus, with the right-hand subpanels, it is possible to observe any trends in degradation. With the left-hand subpanels, it is possible to observe specific points in the lateral span of the web which are producing out-of-tolerance bands, band-spacing or band contrast, which may be caused by clogged pulp applicators.

The data from the photoelectric sensor 14 can also provide information regarding the paper and bands formed thereon, as is discussed at length in the aforementioned U.S.

application Ser. No. 08/893,505, filed on the same date as the instant application, which is incorporated herein by reference. Thus, the output of the photoelectric sensor 14 can be used as a redundant check of the line scan processor 16.

In addition to these graphs, the workstation 330 presents information regarding the roll length, the velocity of the web (from the encoder or a tachometer) and a sample id (which the user enters in advance to label the run). All of the above data can be stored for further non-real-time analysis. The run is indexed by the id number.

The interface software of the workstation 330 additionally includes routines to monitor system parameters to determine system status. When an anomaly is detected, the operator interface will display a message identifying the most-likely cause of the anomaly. In the panel 417 shown in FIG. 18, the message indicates that the lamp 120 (of FIG. 8) is currently functional. The software also controls a 3-color beacon 99 mounted on the inspection station. The beacon flashes red to denote a system failure, yellow to denote an inspection inhibited mode, and green to denote an inspection active mode.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

By way of example, the present invention has been described in the context of detecting bands formed on cigarette paper. But the present invention extends to the detection of any information formed on sheet-like material.

What is claimed is:

1. A rewinder inspection station for inspecting cigarette paper containing banded regions and non-banded regions, comprising:
   an unwind assembly for unwinding an unwind bobbin of said cigarette paper;
   a guiding assembly for guiding said cigarette paper to a camera, said camera forming electrical signals representing properties of said cigarette paper;
   a processor for analyzing said electrical signals to provide analysis results; and
   a rewind assembly for rewinding said cigarette paper on a rewind bobbin after said camera forms said electrical signals of said cigarette paper;
   wherein said processor includes:
   logic for successively examining pixels to determine whether each successive pixel corresponds to a non-banded region or a banded region;
   logic for computing spacing between adjacent banded regions on said cigarette paper based on results provided by said logic for successively examining; and
   logic for computing width of banded regions on said cigarette paper based on results provided by said logic for successively examining.

2. The inspection station of claim 1, wherein the camera includes a linear CCD array.

3. The inspection station of claim 1, wherein said processor's analysis results additionally comprise computation of;
   contrast of banded regions on said cigarette paper.

4. The inspection station of claim 1, wherein said processor periodically transfers said analysis results to a computer, which displays said analysis results.

5. The inspection station of claim 4, wherein said computer aggregates a plurality of reported analysis results, and presents a statistical summary of said analysis results.

6. The inspection station of claim 1, further including an encoder for sensing a speed at which said web is transferred from said unwind bobbin to said rewind bobbin.

7. The inspection station of claim 6, further including a printer for printing information on said paper by reference to output of said encoder.

8. The inspection station of claim 1, wherein said rewind assembly further includes a powered drive wheel which contacts an outer surface of said rewind bobbin, wherein rotation of said drive wheel induces rotation of said rewind bobbin.

9. The inspection station of claim 8, further including a slider assembly for mounting said rewind bobbin such that a center of said rewind bobbin can vary with respect to said drive wheel to accommodate varying diameters of said rewind bobbin.

10. The inspection station of claim 9, further including a device for moving said rewind bobbin on said slider assembly.

11. The inspection station of claim 10, wherein said device for moving said rewind bobbin on said slider assembly comprises an air cylinder.

12. The inspection station of claim 9, wherein said device for moving said rewind bobbin on said slider assembly applies force to said rewind bobbin such that said rewind bobbin is pressed against said drive wheel.

13. A rewinder inspection station for inspecting cigarette paper containing banded regions and non-banded regions, comprising:
   an unwind assembly for unwinding an unwind bobbin of said cigarette paper;
   a guiding assembly for guiding said cigarette paper to a camera, said camera forming electrical signals representing properties of said cigarette paper;
   a processor for analyzing said electrical signals to provide analysis results; and
   a rewind assembly for rewinding said cigarette paper on a rewind bobbin after said camera forms said electrical signals of said cigarette paper;
   wherein said processor includes logic for dividing said electrical signals of said camera into a plurality of lanes, and examining electrical signals within each output lane to determine whether the electrical signals are above or below a threshold, wherein electrical signals above said threshold are indicative of said banded regions, and electrical signals below said threshold are indicative of said non-banded regions of said cigarette paper.

14. The inspection station of claim 13, wherein said threshold is computed as a function of a moving average of gray level values within one or more non-banded regions, and a moving average of relative gray level values within one or more banded regions.

15. A rewinder inspection station for inspecting cigarette paper containing banded regions and non-banded regions, comprising:
   an unwind assembly for unwinding an unwind bobbin of said cigarette paper;
   a guiding assembly for guiding said cigarette paper to a camera, said camera forming electrical signals representing properties of said cigarette paper;
   a processor for analyzing said electrical signals to provide analysis results; and a rewind assembly for rewinding said cigarette paper on a rewind bobbin after said camera forms said electrical signals of said cigarette paper;

wherein said processor discriminates nonbanded regions from banded regions using a dynamic threshold.

16. The inspection station of claim 15, wherein said dynamic threshold is computed as a function of a moving average of gray level values within one or more non-banded regions, and a moving average of relative gray level values within one or more banded regions.

17. A rewinder inspection station for inspecting cigarette paper containing banded regions and non-banded regions, comprising:

an unwind assembly for unwinding an unwind bobbin of said cigarette paper;

a guiding assembly for guiding said cigarette paper to a camera, said camera forming electrical signals representing properties of said cigarette paper;

a processor for analyzing said electrical signals to provide analysis results; and a rewind assembly for rewinding said cigarette paper on a rewind bobbin after said camera forms said electrical signals of said cigarette paper;

wherein said unwind assembly includes:

a shaft;

a backing plate located at one end of said shaft for mounting said unwind bobbin;

a cone for mating with an inner core of said unwind bobbin; and a nut for securing said cone, unwind bobbin and said backing plate in a fixed position relative to each other.

18. The inspection station of claim 17, wherein said shaft includes a terminal threaded end, and said nut can be slid over said threaded end without engaging threads of said threaded end.

19. The inspection station of claim 7, further comprising:

a device for exerting resistance which restricts rotation of said shaft;

a device for determining an amount of tension on said paper as it passes from said unwind bobbin to said rewind bobbin to produce a tension value, and for transmitting said tension value to said device for exerting resistance;

wherein said exerted resistance is a function of said tension value.

20. The inspection station of claim 19, wherein said device for exerting resistance is a magnetic particle brake.

21. The inspection station of claim 19, wherein said device for determining an amount of tension is a strain gauge sensor.

22. A rewinder inspection station for inspecting cigarette paper containing banded regions and non-banded regions, comprising:

an unwind assembly for unwinding an unwind bobbin of said cigarette paper;

a guiding assembly for guiding said cigarette paper to a camera, said camera forming electrical signals representing properties of said cigarette paper;

a processor for analyzing said electrical signals to provide analysis results; and a rewind assembly for rewinding said cigarette paper on a rewind bobbin after said camera forms said electrical signals of said cigarette paper;

wherein said rewind assembly includes:

a shaft;

a backing plate located at one end of said shaft for mounting said rewind bobbin;

a cone for mating with an inner core of said rewind bobbin; and a nut for securing said cone, rewind bobbin and said backing plate in a fixed position relative to each other.

23. The inspection station of claim 22, wherein said shaft includes a terminal threaded end, and said nut can be slid over said threaded end without engaging threads of said threaded end.

24. A method for inspecting paper containing banded regions and non-banded regions, including the steps of:

unwinding said paper from an unwind bobbin;

directing said unwound paper to an inspection station;

at said inspection station, directing light from a light source to the surface of said paper, said light forming reflections from said paper;

receiving said reflections by a camera to generate output signals;

processing said output signals in a processing module to generate output information representative of one or more of the following properties;

width of one or more banded regions;

spacing between one or more adjacent sets of banded regions;

contrast of one or more banded regions; and rewinding said paper on a rewind bobbin after said camera forms said output signals of said paper;

wherein said processing module generates said output information by:

successively examining pixels to determine whether each successive pixel corresponds to a non-banded region or a banded region;

computing spacing between adjacent banded regions on said cigarette paper based on results provided by the step of successively examining; and computing width of banded regions on said cigarette paper based on results provided by the step of successively examining.

25. The method of claim 24, further including the step of periodically transferring said output information to a computer, which displays said output information.

26. The method of claim 25, wherein said computer aggregates a plurality of reported output information, and presents a statistical summary of said output information.

27. A method for inspecting paper containing banded regions and non-banded regions, including the steps of:

unwinding said paper from an unwind bobbin;

directing said unwound paper to an inspection station;

at said inspection station, directing light from a light source to the surface of said paper, said light forming reflections from said paper;

receiving said reflections by a camera to generate output signals;

processing said output signals in a processing module to generate output information representative of one or more of the following properties;

width of one or more banded regions;

spacing between one or more adjacent sets of banded regions;

contrast of one or more banded regions; and rewinding said paper on a rewind bobbin after said camera forms said output signals of said paper;

wherein said processing includes the steps of:

dividing said output signals of said camera into a plurality of lanes; and examining output signals within each lane to determine whether the output signals are above or below a threshold, wherein output signals above said threshold are indicative of said banded regions, and output signals below said threshold are indicative of said non-banded regions of said cigarette paper.

28. The method of claim 27, wherein said threshold is computed as a function of a moving average of gray level values within one or more non-banded regions, and a moving average of relative gray level values within one or more banded regions.

29. A method for inspecting paper containing banded regions and non-banded regions, including the steps of:

unwinding said paper from an unwind bobbin;

directing said unwound paper to an inspection station;

at said inspection station, directing light from a light source to the surface of said paper, said light forming reflections from said paper;

receiving said reflections by a camera to generate output signals;

processing said output signals in a processing module to generate output information representative of one or more of the following properties;

width of one or more banded regions;

spacing between one or more adjacent sets of banded regions;

contrast of one or more banded regions; and rewinding said paper on a rewind bobbin after said camera forms said output signals of said paper;

wherein said processing includes the step of discriminating non-banded regions from banded regions using a dynamic threshold.

30. The method of claim 29, wherein said dynamic threshold is computed as a function of a moving average of gray level values within one or more non-banded regions, and a moving average of relative gray level values within one or more banded regions.

31. A rewinder inspection station for inspecting sheet-like material, comprising:

an unwind assembly for unwinding an unwind bobbin of said sheet-like material;

a guiding assembly for guiding said sheet-like material to a camera, said camera forming electrical signals representing properties of said sheet-like material;

a processor for analyzing said electrical signals to provide analysis results;

and a rewind assembly for rewinding said sheet-like material on a rewind bobbin after said camera forms said electrical signals of said sheet-like material;

wherein said unwind assembly and said rewind assembly each include:

a shaft;

a backing plate located at one end of said shaft for mounting a bobbin;

a cone for mating with an inner core of the bobbin; and a nut for securing said cone, bobbin and said backing plate in a fixed position relative to each other.

32. The rewinder inspection station of claim 31, wherein said shaft includes a terminal threaded end, and said nut has a bore which can receive the shaft in two different angular orientations, such that said nut can be slid over said threaded end without engaging threads of said threaded end in one of said orientations.

33. A rewinder inspection station for inspecting sheet-like material, comprising:

an unwind assembly for unwinding an unwind bobbin of said sheet-like material;

a guiding assembly for guiding said sheet-like material to a camera, said camera forming electrical signals representing properties of said sheet-like material;

a processor for analyzing said electrical signals to provide analysis results;

and a rewind assembly for rewinding said sheet-like material on a rewind bobbin after said camera forms said electrical signals of said sheet-like material;

wherein said rewind assembly further includes a powered drive wheel which contacts an outer surface of said rewind bobbin, wherein rotation of said drive wheel induces rotation of said rewind bobbin.

34. The rewinder inspection station according to claim 33, further including a slider assembly for mounting said rewind bobbin such that a center of said rewind bobbin can vary with respect to said drive wheel to accommodate varying diameters of said rewind bobbin.

* * * * *